United States Patent
Hermann et al.

(10) Patent No.: US 9,957,532 B2
(45) Date of Patent: May 1, 2018

(54) FERMENTATION PROCESS FOR THE PRODUCTION OF ORGANIC ACIDS

(71) Applicant: Myriant Corporation, Woburn, MA (US)

(72) Inventors: Theron Hermann, Arlington, MA (US); James Reinhardt, Columbus, OH (US); Xiaohui Yu, Woburn, MA (US); Russell Udani, Somerville, MA (US); Lauren Staples, Wilmington, MA (US)

(73) Assignee: Myriant Corporation, Woburn, MA (US)

( * ) Notice: Subject to any disclaimer, the term of this patent is extended or adjusted under 35 U.S.C. 154(b) by 139 days.

(21) Appl. No.: 14/702,187

(22) Filed: May 1, 2015

(65) Prior Publication Data

US 2016/0319309 A1    Nov. 3, 2016

(51) Int. Cl.
   *C12P 7/46*   (2006.01)

(52) U.S. Cl.
   CPC ..................... *C12P 7/46* (2013.01)

(58) Field of Classification Search
   CPC ........................................................ C12P 7/46
   See application file for complete search history.

(56) References Cited

U.S. PATENT DOCUMENTS

| | | | |
|---|---|---|---|
| 5,168,055 A | 12/1992 | Datta | |
| 5,958,744 A | 9/1999 | Berglund | |
| 6,117,404 A | 9/2000 | Mimura | |
| 6,270,731 B1 | 8/2001 | Kato | |
| 6,455,284 B1 | 9/2002 | Gokarn | |
| 6,524,843 B1 | 2/2003 | Blais | |
| 6,908,507 B2 | 6/2005 | Lalande | |
| 7,070,967 B2 | 7/2006 | Dale | |
| 7,223,567 B2 | 5/2007 | Ka-Yiu | |
| 7,223,576 B2 | 5/2007 | Hartley | |
| 7,232,664 B2 | 6/2007 | Van Hoek | |
| 7,244,610 B2 | 7/2007 | San | |
| 7,256,016 B2 | 8/2007 | San | |
| 7,262,046 B2 | 8/2007 | Ka-Yiu | |
| 7,514,056 B2 | 4/2009 | Fradette | |
| 7,563,606 B2 | 4/2009 | Aoyama | |
| 7,596,952 B2 | 7/2009 | Fradette | |
| 7,608,439 B2 | 10/2009 | McTavish | |
| 2006/0073577 A1 | 4/2006 | Bennett | |
| 2006/0185519 A1 | 8/2006 | Bender | |
| 2006/0193765 A1 | 8/2006 | Arima | |
| 2006/0205048 A1 | 9/2006 | Aoyama | |
| 2007/0111294 A1 | 5/2007 | Burgard | |
| 2008/0072496 A1 | 3/2008 | Gamzon | |
| 2008/0293113 A1 | 11/2008 | Fukui | |
| 2009/0162914 A1 | 6/2009 | McTavish | |
| 2009/0170174 A1 | 7/2009 | Bolkan | |
| 2009/0186392 A1 | 7/2009 | Gonzalez | |
| 2010/0051859 A1 | 3/2010 | Aziz | |
| 2010/0092359 A1 | 4/2010 | Svendsen | |
| 2013/0130339 A1* | 5/2013 | Hermann | .................. C12P 7/46 435/145 |

* cited by examiner

*Primary Examiner* — Maryam Monshipouri
(74) *Attorney, Agent, or Firm* — Ramasamy M. Mannan

(57) ABSTRACT

This invention relates to improvements in the fermentation process used in the production of organic acids from biological feedstock using bacterial catalysts. The improvements in the fermentation process involve providing a fermentation medium comprising an appropriate form of inorganic carbon, an appropriate amount of aeration and a biocatalyst with an enhanced ability to uptake and assimilate the inorganic carbon into the organic acids. This invention also provides, as a part of an integrated fermentation facility, a novel process for producing a solid source of inorganic carbon by sequestering carbon released from the fermentation in an alkali solution.

16 Claims, 14 Drawing Sheets

FERMENTATION PROCESS FOR THE PRODUCTION OF ORGANIC ACIDS

GOVERNMENT SUPPORT

The invention was made with United States government support under a contract awarded from the US Department of Energy under Award Number DE-EE0002878/001. The United States government has certain rights in the invention.

CROSS-REFERENCE TO RELATED APPLICATIONS

The application is a divisional application of U.S. application Ser. No. 13/812,886, filed on Jan. 29, 2013 which is the U.S. national stage application of International Patent Application No. PCT/US2011/046047 filed on Jul. 30, 2011, which claims the priority of the U.S. Provisional Application Ser. No. 61/400,596, filed on Jul. 31, 2010.

BACKGROUND OF THE INVENTION

A 2004 U.S. Department of Energy report entitled "Top value added chemicals from biomass" has identified twelve building block chemicals that can be produced from renewable feedstocks. The twelve sugar-based building block chemicals are 1,4-diacids (succinic, fumaric and maleic), 2,5-furan dicarboxylic acid, 3-hydroxy propionic acid, aspartic acid, glucaric acid, glutamic acid, itaconic acid, levulinic acid, 3-hydroxybutyrolactone, glycerol, sorbitol, and xylitol/arabinitol.

Building block chemicals are molecules with multiple functional groups that possess the potential to be transformed into new families of useful molecules. The twelve building blocks identified by U.S. Department of Energy can be subsequently converted to a number of high-value biobased chemicals or materials.

During the last few years a number of microorganisms have been created through genetic engineering for the production of industrially useful monomeric building block chemical compounds. Many natural metabolites derived from biological fermentative processes such as dicarboxylic acids, amino acids, and diols have functional groups that are suitable for polymerization and chemical synthesis of industrially useful polymers.

In recent years attention has been focused on reducing the cost of production of industrially useful chemical compounds through biological fermentation. One well known approach for reducing the cost of fermentative production of chemical compounds is to use low-cost minimal medium in place of expensive nutritionally rich medium. For example, the *E. coli* strain described in U.S. Pat. No. 7,223,567 requires a rich medium supplemented with glucose as the source of carbon for the production of succinic acid. The *E. coli* strain KJ122 useful for the production of succinic acid described by Jantama et al (2008a and 2008b) and in the PCT Patent Application Publications Nos. WO/2008/021141A2 and WO/2010/115067 is capable of growth on a minimal medium without the need for any expensive ingredients such as yeast extract or tryptone. Another approach that is being attempted to further reduce the cost of fermentative production of chemical compounds is to replace the currently used expensive feedstocks such as dextrose and sucrose with cheaper organic carbon source such as a mixture of six-carbon and five-carbon sugars derived form lignocellulosic biomass through a pretreatment process.

The inventors have discovered a novel method for further reducing the cost of producing specialty chemicals through biological fermentation. This new method for improving the productivity and the yield of succinic acid through a biological fermentation process is based on the observation that the yield and productivity of succinic acid in the biological fermentation process requires the supply of both organic carbon and inorganic carbon sources. A reduction in the cost of production of succinic acid can be achieved by means of supplying the required inorganic carbon in a cost effective manner besides meeting the requirement for organic carbon sources.

As defined in this invention, the term organic carbon refers to the organic feedstocks such as xylose, glucose, glycerol and sucrose useful for the fermentative production of organic acid by the microorganism. The term inorganic carbon refers to the carbon dioxide present in the gas phase of the fermentation chamber and the carbonate and bicarbonate salts added as a component of the fermentation medium.

The importance of the contribution from inorganic carbon towards succinic acid production by microbial catalysts is now well established although the relative contribution of inorganic and organic carbon fractions to the final succinic acid production is not precisely established.

While the transformation of organic carbon into succinic acid is achieved by the modification of the central metabolic pathway including the glycolytic pathway and the tricarboxylic acid cycle within the cell, the incorporation of inorganic carbon into succinic acid requires the participation of carboxylating enzymes. At least four different types of carboxylating enzymes are known to be functional within bacterial cells. The phosphoenol pyruvate carboxylase (PEBcase or PPC) carboxylates phosphoenol pyruvate leading to the formation of oxaloacetic acid. The malic enzyme carboxylates pyruvic acid leading to the formation of malic acid and requires reduced cofactors such as NADH or NADPH. The third carboxylating enzymes known as pyruvate carboxlase (PYC) carboxylates pyruvic acid to produce oxaloacetic acid. The fourth carboxylating enzyme known as phosphoenolpyruvate carboxykinase (PCK) carboxylates phosphoenol pyruvate to oxaloacetate with the production of one molecule of ATP for every molecule of oxaloacetate produced from the carboxylation of a phosphoenol pyruvate molecule. The inorganic carbon assimilated through the carboxylation reactions mediated by one of these four different carboxylating enzymes present within a bacterial cell contributes to the carbon back bone of the succinic acid produced through fermentation process.

The *E. coli* strains currently in use for the production of succinic acid are reported to have enhanced activity for one or other carboxylating enzymes. U.S. Pat. No. 6,455,284 discloses the use of an exogenous pyruvate carboxylase enzyme for enhancing the production of oxaloacetate-derived chemicals through fermentation. Expression of *Rhizobium etli* pyruvate carboxylase gene in *E. coli* cells caused an increased carbon flow towards oxaloacetate in wild type *E. coli* cells without affecting the glucose uptake rate or the growth rate and restored succinate formation in *E. coli* phosphoenolpyruvate carboxylase null mutants. Zhang et al (2009) have reported that in KJ122 strain of *E. coli* due to a mutation in the promoter region, the phosphoenolpyruvate carboxykinase enzyme shows enhanced carboxylation capacity.

Sanchez et al (2005) have reported that the flux to the oxaloacetate pool was increased by overexpressing the enzyme pyruvate carboxylase (PYC) from *Lactococcus lac-* tis in *E. coli* cells. The synthesis of oxaloacetate is a key step towards the synthesis of succinate. In wild-type *E. coli* phosphoenol pyruvate carboxylase represents the principle anaplerotic reaction to replenish oxaloacetate. Under anaerobic conditions the portion of phosphoenolpyruvate not flowing to oxaloacetate is converted to pyruvate. In strains not expressing the heterologous pyruvate carboxylase, pyruvate was observed to accumulate and succinate yield decreased compared to the strain overexpressing pyruvate carboxylase.

Lin et al (2005) have shown that the highest level of succinate production in *E. coli* can be achieved by expressing both phosphoenol pyruvate carboxylase from *Sorghum vulgare* and pyruvate carboxylase from *Lactococcus lactis* when compared to *E. coli* strains individually overexpressing either phosphoenol pyruvate carboxylase or pyruvate carboxylase.

As indicated by these studies, all the efforts so far have been focused on increasing the succinic acid production capability by means of effectively utilizing the inorganic carbon already present within the cell. This present invention provides a novel method for enhancing the inorganic carbon uptake by bacterial cells leading to an increase in the concentration of inorganic carbon within the bacterial cell with the ultimate goal of increasing the succinic acid production.

Generally, the inorganic carbon requirement for the fermentative production of succinic acid is supplied either in the form gaseous carbon dioxide or in the form of a carbonate salt such as sodium carbonate, sodium bicarbonate, ammonium carbonate, and ammonium bicarbonate. A number of US patents have disclosed the use of inorganic carbon either to maintain the pH of the culture medium or to maintain the growth rate of the microorganism. For example, U.S. Pat. No. 5,958,744 uses $NaHCO_3$ to neutralize the succinic acid produced by the *E. coli* strain AFP 111. The sodium bicarbonate addition to the fermentation medium besides maintaining the neutral pH, also serves as a source of inorganic carbon required for the carboxylation reactions within the cell. Andersson (2007) has demonstrated that the use of $Na_2CO_3$ as a neutralizing agent is desirable over the use of $NH_4OH$, KOH, and NaOH as neutralizing agents. It has been reported that $NH_4OH$ as a neutralizing agent is toxic to *E. coli* and could cause a decrease in the viability of the cells and the succinate productivity (Andersson et al., 2009). Thus the prior art teaches away from the use of $NH_4OH$ as the neutralizing agent in the succinic acid production.

Andersson et al (2007) have disclosed the use of gaseous carbon dioxide in the production of succinic acid using the metabolically engineered *E. coli* strains AFP 111 and AFP184. These succinic acid producing strains were grown in a medium maintained at pH between 6.6 and 6.7 with the addition of $NH_4OH$ as 15% $NH_3$ solution. The anaerobic production phase was initiated by withdrawing the air supply and sparging the culture medium with $CO_2$ at a flow rate of 3 L min$^{-1}$.

U.S. Pat. No. 5,168,055 discloses that the growth conditions for succinic acid producing *Anaerospirillum succiniproducens* requires at least about 0.1 atmospheric $CO_2$. The medium can be sparged with $CO_2$ gas. The fermentation can be run in a pressurized reactor which contains $CO_2$ at super atmospheric pressure. The $CO_2$ can be mixed with other gases as long as the gases employed do not interfere with the growth. Carbon dioxide can also be supplied to the fermentation medium by the addition of carbonate or bicarbonate salts which generates $CO_2$ gas under the conditions of the fermentation. For sufficient succinic acid production, the medium should contain dissolved CO2 in equilibrium.

Promising succinic acid producing bacteria *Mannheimia succinciproducens* and *Actinobacillus succinogens* have been isolated from bovine rumen. The major gas produced in the rumen of the cattle is $CO_2$ (65.5 mol %). These strains of rumen bacteria are capnophilic ($CO_2$ loving) and produce succinic acid as the major product from various carbon sources under 100% $CO_2$ conditions at pH of 6.0 to 7.5. Genome-scale metabolic flux analysis indicated that $CO_2$ is important for the carboxylation of phosphoenolpyruvate to oxaloacetate, which is converted to succinic acid by the reductive tricarboxylic acid cycle (Lee et al., 2002; Hong et al., 2004; Song and Lee., 2006).

Song et al (2007) have shown that in the capnophilic rumen bacterium *M. succiniproducens* the production of succinic acid by a carboxylation reaction during fermentation is dependent on intracellular $CO_2$. They investigated the metabolic responses of *M. succiniproducens* to the different dissolved $CO_2$ concentrations (0-260 mM). Cell growth was severely suppressed when the dissolved $CO_2$ concentration was below 8.74 mM. The cell growth and succinic acid production increased proportionally as the dissolved $CO_2$ concentration increased from 8.74 to 141 mM. The yields of biomass and succinic acid on glucose obtained at the dissolved $CO_2$ concentration of 141 mM were 1.49 and 1.52 times higher respectively, than those obtained at the dissolved $CO_2$ concentration of 8.74 mM. It was also found that the addition of $CO_2$ source provided in the form of $NaHCO_3$, $MgCO_3$, or $CaCO_3$ had positive effects on cell growth and succinic acid production. However, growth inhibition was observed when excessive bicarbonate salts were added. By the comparison of the activities of key enzymes, it was found that phosphoenol pyruvate carboxylation by phosphoenol pyruvate carboxykinase is most important for succinic acid production as well as the growth of *M. succiniproducens* by providing additional ATP.

U.S. Pat. No. 7,223,576 discloses the use of both sodium bicarbonate and gaseous carbon dioxide in the production of succinic acid by a mutant *E. coli* strain with the heterologous pyruvate carboxylase gene from *Lactococcus lactis*. The pH of the growth medium was maintained with 1.0 M $Na_2CO_3$ and $CO_2$ gas was sparged through the culture during the fermentation period at a constant flow rate. The heterolgus expression of pyruvate carboxylase in a succinate producing strain of *E. coli* increases the carbon flux from pyruvate to oxaloacetic acid. Pyruvate carboxylase diverts pyruvate toward oxaloacetic acid to favor succinate generation.

U.S. Pat. No. 7,244,610 discloses the aerobic succinate production using a bacterial catalyst. The growth medium contained 2 g/L $NaHCO_3$ and approximately 60 mM glucose. $NaHCO_3$ was added to the culture medium because it yielded better cell growth and succinate production due to its pH-buffering capacity and its ability to supply $CO_2$.

U.S. Pat. No. 7,262,046 discloses a growth medium containing 2 g/L $NaHCO_3$ in the aerobic succinate production using a bacterial biocatalysts. The washed culture was then used to inoculate a bioreactor containing LB with 2 g/L $NaHCO_3$.

US Patent Application Publication No. 2006/0073577 A1 discloses the use of LB broth medium supplemented with 20 g/L of glucose, and 1 g/L of $NaHCO_3$ in the production of succinate. $NaHCO_3$ was added to the culture medium because of its pH-buffering capacity and its ability to supply $CO_2$.

US Patent Application No. 2009/0186392 A1 discloses a method of glycerol fermentation where pH and $CO_2$ concentrations are controlled to allow the fermentative metabolism of glycerol to desired chemical precursors. $CO_2$ concentrations were inevitably linked to pH and went down as pH increased because $CO_2$ was converted to bicarbonate. By increasing $CO_2$ to 20-30% the negative effects of increased pH above 7.0 could be reduced. Improved glycerol fermentation was seen with pH 6.3 and 10% $CO_2$, and with pH 7.5 and 20% $CO_2$. Greater concentrations of $CO_2$ were also beneficial.

U.S. Pat. No. 7,256,016 discloses a recycling system for manipulation of intracellular NADH availability. The anaerobic tube experiments were performed using 40 ml or 45 ml glass vials with open top caps and PTFE/silicone rubber septa. Each vial was filled with 35 ml or 40 ml of LB medium supplemented with 20 g/L glucose, 100 mg/L kanamycin, 0 or 50 mM formate and 1 g/L $NaHCO_3$ to reduce the initial lag time that occurs under anaerobic conditions.

In a dual phase growth pattern for production of succinate, the bacterial culture is initially grown in an aerobic condition and transferred to an anaerobic production phase. The succinate production occurs during the anaerobic growth phase. No growth occurs during the anaerobic process. Glucose consumption and product formation rates were essentially constant under anaerobic conditions and the process exhibits a metabolic pseudo-steady-state. The anaerobic biocatalytic process for the production of succinic acid has been shown to consume carbon dioxide under non-growing anaerobic conditions. Since $CO_2$ is incorporated into the carbon backbone as a result of the carboxylation of phosphoenol pyruvate by phosphoenol pyruvate carboxylase, it is hypothesized that different $CO_2$ concentrations in the gas phase would impact the metabolic fluxes and ultimately change the yield and rate of succinate generated. The effect of $CO_2$ on succinate production in dual-phase *Escherichia coli* fermentation is well documented (Lu et al., 2009).

International patent application WO 2009/083756 A1 published under the Patent Cooperation Treaty provides a large scale microbial culture method for producing succinic acid using a recombinant bacteria containing an over expressed pyruvate carboxylase gene. The culture is initially grown aerobically in a medium devoid of any inorganic carbon. After the growth in the aerobic environment, the bacterial culture is acclimatized to oxygen lean condition wherein the oxygen concentration is brought down to less than 5% oxygen in the reactor by means of purging the with $CO_2$ or $CO_2$ mixed with an inert gas. The carbon dioxide thus supplied provides the source of inorganic carbon required by the pyruvate carboxylase enzyme.

In the experiments with *E. coli* stain AFP111, it has been shown that when the concentration of $CO_2$ in the gas phase is increased from 0% to 50%, the succinate specific productivity increased from 1.9 mg/g·h to 225 mg/g·h and the succinate yield increased from 0.04 g/g to 0.75 g/g. Above 50% $CO_2$ concentration in the medium, succinate production did not increase further. A four-process explicit model to describe the $CO_2$ transfer and utilization has predicted that at $CO_2$ concentration below about 30-40%, the system becomes limited by gas phase $CO_2$, while at higher $CO_2$ concentrations the system is limited by phosphoenol pyruvate carboxylase enzyme kinetics. At limiting $CO_2$ concentrations, the succinic acid production can be rate limited at different stages. The diffusion of $CO_2$ from the gas phase into the liquid phase may be limiting. As a result of poor equilibrium, the concentration of the $CO_2$ in the liquid phase may be several folds lower than the concentration of $CO_2$ in the gas phase. Another step in the availability of $CO_2$ lies at the transfer of the dissolved $CO_2$ from the exterior liquid phase to the interior of the biocatalysts. The diffusion of dissolved $CO_2$ through the cell membrane may be too slow. Even the permeation of $HCO_3$ through the cell membrane may be insignificant. Once inside the cell, the $CO_2$ is converted into bicarbonate [$HCO_3^-$] form so that it can be used as a substrate for the functioning of the phosphoenol pyruvate carboxylase. The conversion of $CO_2$ to bicarbonate is mediated by carbonic anhydrase (Lu et al., 2009).

U.S. Pat. No. 6,455,284 discloses a dual-phase *E. coli* fermentation for the production of succinic acid. The *E. coli* strain used in this study contained a polynucleotide sequence encoding a pyruvate carboxylase operatively linked to a promoter, wherein said polynucleotide sequence is expressed and produces an enzymatically active pyruvate carboxylase which is able to incorporate the inorganic carbon in the growth medium into the succinic acid produced. *E. coli* cells were grown aerobically in Luria-Bertani (LB) medium. Anaerobic fermentation were carried out in 100 ml serum bottles with 50 ml LB medium supplemented with 20 g/L glucose and 40 g/L $MgCO_3$. The fermentations were terminated at 24 hours at which point the pH value of all fermentations were approximately pH 6.7.

US Patent Application Publication No. 2007/0111294 provides growth coupled succinate production in *E. coli* strains. All experiments were performed using M9 minimal medium at pH 7.0 (6.78 g/L $Na_2HPO_4$, 3.0 g/L $KH_2PO_4$, 0.5 g/L NaCl, 1.0 g/L $NH_4Cl$, 1 mM $MgSO4$, 0.1 mM $CaCl_2$) supplemented with 2 g/L glucose and 20 mM $NaHCO_3$. The inorganic carbon required for the succinic acid production was provided by $NaHCO_3$ in the medium.

U.S. Pat. No. 7,563,606 provides a method for producing succinic acid using the bacterial strain *Brevibacterium flavum* MJ-233. *Brevibacterium flavum* may be currently classified into *Corynebacterium glutamicum*. These bacterial cells showed an enhanced pyruvate carboxylase activity due to the presence of a plasmid coding for the pyruvate carboxylase activity. The neutralization was carried out by using magnesium carbonate and magnesium hydroxide. Supplementing the magnesium carbonate either with ammonium hydrogen carbonate or sodium hydrogen carbonate enhanced the succinic acid production rate and yield. $CO_2$ gas was also provided to the fermentation vessel. Apparently, the $CO_2$ gas and various carbonate and bicarbonate salts acted as the source of the inorganic carbon required for the action of pyruvate carboxylase enzyme contributing the flow of carbon towards succinic acid.

US Patent Application Publication Nos. 2006/0205048 and 2008/0293113 provide a method for producing succinic acid in a medium containing carbonate ion, bicarbonate ion or carbon dioxide gas and a bacterial strain containing enhanced levels of pyruvate carboxlase enzyme. The suitable bacterial strains are derived from a group consisting of *Coryneform* bacterium, *Bacillus* bacterium, and *Rhizopium* bacterium.

As described above, each of the microbial catalyst currently in use for the production of succinic acid is known to require a source of inorganic carbon for efficient production of succinic acid. In view of the importance of the inorganic carbon in the production of succinic acid, the present invention provides a novel method for preparing solid inorganic carbonate and bicarbonate salts by means of sequestering the carbon released from various industrial applications. The carbon released from fossil fuel burning and the operation of fermentation facilities can be trapped in alkali solutions and the resulting carbonate and bicarbonate salts can be used as a source of inorganic carbon in the fermentative production of succinic acid. In addition, the present invention provides a method for using the product resulting from the sequestration of carbon dioxide.

BRIEF SUMMARY OF THE INVENTION

This invention is applicable to all industrial microbiological process wherein the productivity and the yield of end products are dependent on the uptake and utilization of inorganic carbon from the medium. In particular, the present invention is suitable for the production of organic acid thorough anaerobic fermentation process. More specifically, the present invention is useful in reducing the cost of production of succinic acid through anaerobic fermentation process and in helping the global carbon sequestration efforts.

In one embodiment, the present invention provides a method for sequestering the carbon dioxide released during the fermentation process. The utilization of carbon dioxide gas as a source of inorganic carbon in the fermentation solution is very inefficient. The solubility of carbon dioxide in aqueous solution is several folds lower when compared to the concentration in the gas phase. Moreover, the continuous pumping of carbon dioxide into the fermentation vessel results in the release of carbon dioxide into the atmosphere. The present invention overcomes this limitation by means of supplying the required inorganic carbon in the form of carbonate or bicarbonate salts which is obtained by trapping the carbon dioxide gas released from the fermentation vessel in alkali solution.

In one aspect, the present invention provides a cost effective carbonate or bicarbonate salts suitable for the biological production of succinic acid. The present invention shows that the expensive $K_2CO_3$ and KOH used in the fermentation process can be replaced with relatively inexpensive $NH_4OH$. In another aspect, the present invention provides a means of cost saving by means of using $NH_4HCO_3$ as a source of inorganic carbon in place of $K_2CO_3$ and $KHCO_3$. $NH_4HCO_3$ besides serving as a source of inorganic carbon can also act as a source of nitrogen.

In yet another embodiment of the present invention, the microbial culture is provided with microaeration during the production phase of its growth. In one aspect of the present invention, microaeration is provided in order to assure that there is a complete consumption of the organic carbon supply in the medium. In another aspect of the present invention, an appropriate amount of microaeration is provided to increase the titer and the productivity of succinic acid.

These fermentation process improvements can be utilized both in the batch mode of fermentation and fed-batch mode of fermentation. Moreover, these fermentation process improvements can be practiced with a variety of microbial biocatalyst utilizing starch and lignocellulosic hydrolysates derived from renewable resources.

Additional advantage of this invention will become readily apparent from the ensuing description.

DETAILED DESCRIPTION OF THE PREFERRED EMBODIMENTS

Figure 1:
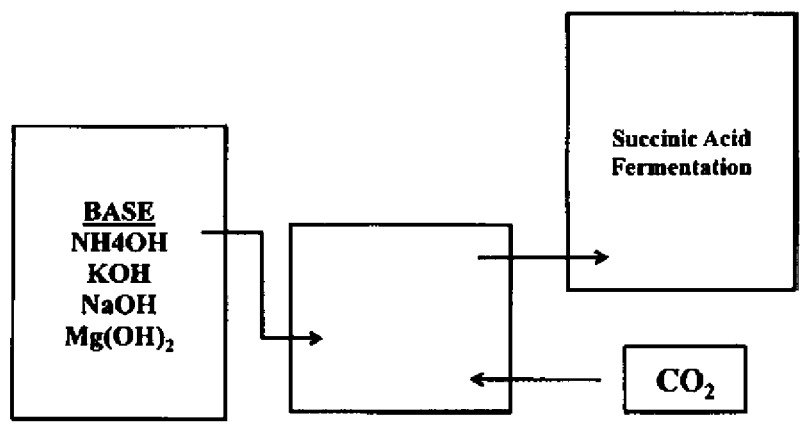
FIG. 1. Process flow diagram for generating bicarbonate salts useful as a source of inorganic carbon in the fermentative production of succinic acid. As explained in Example 1, any one of the commonly available alkali solutions such as ammonium hydroxide, sodium hydroxide or potassium hydroxide is added to a vessel and carbon dioxide gas is micro-sparged. The alkali solution inside the container is stirred at 500 rpm for an hour. At the end of one hour, the resulting white slimy liquid is appropriately diluted and used in the microbial fermentation of organic carbon compounds leading to the production of succinic acid.

The present invention provides a process for the production of organic acids in commercially significant quantities from the fermentation of carbon compounds by recombinant microorganisms. More specifically, this present invention provides the fermentation parameters and the biocatalysts suitable for the production of succinic acid at a higher yield. The biocatalysts and the fermentation parameters of the present invention also result in an increased productivity of the succinic acid. The term "yield" as defined in this invention refers to ratio of grams of organic acid produced per gram of organic carbon consumed. The term "productivity" as defined in this invention refers to the actual yield of succinic acid produced and is expressed in terms of number of grams of organic acid produced per liter per hour. The term "normalized yield" as defined in this invention refers to the ratio of moles of organic acid produced per mole of organic carbon consumed wherein the ratio is determined after factoring the dilution that results from the addition of neutralizing agent and other reagents to the fermentor. The biocatalysts of the present invention possess the ability to enhance the inorganic carbon uptake and utilization besides having ability to use multiple sugars in the fermentation process for the production of commercially significant quantities of organic acid.

The enhanced ability for inorganic carbon uptake can be achieved by means of genetic modification. Genetic modification leading to an enhanced ability for inorganic carbon uptake involves introducing genes coding for bicarbonate transporters form eukaryotic and prokaryotic photosynthetic microorganism into the biocatalysts developed for the production of succinic acid (Price at al., 2008; Spalding, 2008). For examples, the genes for bicarbonate transporters can be introduced into the KJ122 strain of *E. coli* developed for the commercial production of succinic acid. The genes coding for bicarbonate transporters can be introduced into the KJ122 strain in the form of a self-replicating plasmid with genes coding for the bicarbonate transport proteins under the control of promoters functional in the KJ122 strain. Alternatively, the genes coding for bicarbonate transporters can be integrated into the chromosomal DNA of KJ122 under the control of promoter functional in KJ122.

The enhanced ability for utilizing inorganic acid can be achieved by means of genetic modifications leading to an enhanced activity of one or more carboxylating enzymes within the biocatalysts selected for the commercial production of succinic acid. In a preferred embodiment, the activity of one of the carboxylating enzyme present within the biocatalyst selected for succinic acid production is enhanced by genetic manipulations. For example, the activity of the phosphoenol pyruvate carboxykinase enzyme present within the *E. coli* based bacterial biocatalyst can be enhanced by mean of introducing mutations in the promoter region of the gene coding for this enzyme. Alternatively, the genes coding for carboxylating enzymes such as pyruvate carboxylase or phosphoenolpyruvate carboxylase can be derived from exogenous sources and introduced into the bacterial biocatalysts selected for the production of succinic acid.

The requirement for inorganic carbon in the fermentative production of organic acids such as succinic acid is now well established and the required inorganic carbon can be supplied either in the form of pure gaseous carbon dioxide or carbon dioxide gas mixed with other gases. The carbon dioxide gas either alone or mixed with other gases can be sparged through the fermentation fluid. Alternatively, the inorganic carbon can be supplied in the form of carbonate or bicarbonate salts of various alkali and alkaline earth metals such as $K_2CO_3$, $KHCO_3$, $Na_2CO_3$, $NaHCO3$, $(NH_3)_2CO_3$ and $NH_4HCO3$. It is well known in the art that depending on the pH of the medium, there is definite ratio between the $CO_3^{-2}$, $HCO_3^{-1}$, and $H_2CO_3$ and the corresponding cations. In a preferred embodiment, $NH_4HCO_3$ is used as the source of inorganic carbon. As used in the present invention, the terms ammonium bicarbonate and ammonium hydrogen carbonate are synonyms.

The supply of inorganic carbon in the form of carbonate or bicarbonate salts of alkali and alkaline earth metals is preferred over the supply of gaseous carbon dioxide as the solid form of inorganic carbon increases the inorganic carbon concentration in the fermentation medium beyond what could be achieved by the continuous supply of carbon dioxide gas to the fermentation medium in a cost effective way. Moreover, the use of bicarbonate salt in place of gas phase $CO_2$ also eliminates the issue related to the poor diffusion of $CO_2$ from the gas phase into the aqueous phase.

The solid form of inorganic carbon such as carbonate and bicarbonate salts of alkali metal and alkaline earth metals required for the fermentative production of organic acid may be obtained from commercial sources. In a preferred embodiment, the solid inorganic carbon source is prepared by means of sparging carbon dioxide containing gas through an alkali solution. Either a pure carbon dioxide gas or a flue gas emanating from fossil fuel based power generators or waste gases from large scale industrial fermentation tanks can be sparged through the alkali solutions such as ammonium hydroxide, potassium hydroxide, magnesium hydroxide and sodium hydroxide under pressure and constant stirring till precipitation begins (FIG. 1). In a preferred embodiment, the carbon dioxide emanating from the fermentation vessel is pumped through the ammonium hydroxide solution. Trapping the carbon dioxide gas coming from the fermentation vessel in an alkali solution and utilizing the resulting carbonate salts as a source of inorganic carbon in the fermentation constitutes a part of an integrated fermentation facility. In the most preferred embodiment, the carbon dioxide gas emanating from a fermentation facility is sparged into a tank containing 19%-28% $NH_4OH$ solution leading to the production of saturated solution of ammonium bicarbonate. The saturation level of ammonium bicarbonate solution is reached when the concentration of ammonium bicarbonate in the solution reached approximately 3M. By means of starting with ammonium hydroxide solution of different molar concentrations, it is possible to obtain solutions containing specific ratio for ammonium hydroxide and ammonium bicarbonate.

The carbon dioxide used for the preparation of inorganic carbon solids can be derived from the same fermentation vessel where the carbonate salt resulting from carbon dioxide capture ends up. Alternatively, the carbon dioxide gas can be derived from a different fermentation vessel or from a different fermentation plant. For example, the carbon dioxide gas released from an ethanol plant can be captured in an alkali solution and the resulting solid carbonate can be used as a source of inorganic carbon in a succinic acid plant. Even aerobic fermentations such as those producing antibiotics and vitamins and releasing both oxygen and carbon dioxide could be utilized because carbon dioxide would be trapped in the alkali solution while oxygen would leave the alkali trap. The list of the solid inorganic carbons suitable for the present invention includes sodium carbonate, sodium bicarbonate, potassium carbonate, potassium bicarbonate, magnesium carbonate, magnesium bicarbonate, ammonium carbonate, and ammonium bicarbonate. Among these solid inorganic carbon compounds, ammonium carbonate and ammonium bicarbonate are preferred inorganic carbon sources.

In the commercial scale manufacturing of organic acid using biological feedstock and inorganic carbon sources, it is necessary to control the inhibitory effect of organic acid being produced on the viability of the bacterial cells. Therefore it is necessary to add a neutralizing agent to the culture medium for the purpose of neutralizing the organic acid being produced. The pH of the culture vessel can be continuously monitored using a pH probe, and appropriate base can be added to maintain the pH of the growth medium around neutral pH. The list of bases suitable for maintaining the pH of the microbial culture includes, but not limited to NaOH, KOH, $NH_4OH$, $Mg(OH)_2$, $Na_2CO_3$, $NaHCO_3$, and $(NH_4)HCO_3$, $(NH_4)_2CO_3$. The bases suitable for this purpose can be used alone or in combination. In a preferred embodiment, the alkali solution used to trap the gaseous carbon in the production of solid inorganic carbon can also act as a neutralizing agent.

One requirement in selecting the neutralizing base in the commercial scale manufacturing of organic acid is to select a base which is low-cost and compatible with the biocatalysts being used and the recovery process for organic acid. At laboratory scale, the succinic acid neutralization has been achieved using a combination of 1.2 M KOH and 2.4 M $K_2CO_3$. The potassium salts are too expensive to use in the large scale commercial manufacturing. Since NaOH is a low-price commodity chemical, sodium bases such as NaOH and $Na_2CO_3$ are preferred neutralizing bases for the large commercial scale manufacturing of organic acid through biological fermentation. According to the present invention, ammonium hydroxide is the most preferred base for maintaining the pH of the fermentation vessel due to low cost and for the other reasons given below.

Ammonium succinate is accumulated when the $NH_4OH$ and $NH_4HCO_3$ are used as the source of neutralizing base and the source of inorganic carbon respectively in the fermentation medium for the production of succinic acid. The ammonium succinate resulting from the use $NH_4HCO_3$ and $NH_4OH$ is treated with sulfuric acid in the recovery of succinic acid with the resulting formation of ammonium sulfate as a byproduct. Alternatively, the ammonium succinate solution can be passed through an ion-exchange resin and split into succinic acid and an ammonium salt. The large volume ammonium sulfate byproduct resulting from the commercial manufacture of succinic acid can be sold as a fertilizer and thereby account for a significant cost recovery. With the replacement of $K_2CO_3$ and KOH by $NH_4HCO_3$ and $NH_4OH$, the cost of the neutralizing agent for producing a pound of succinic acid is reduced substantially as the price of $NH_4OH$ in the commercial market is much lower than KOH and $K_2CO3$. It is also possible to synthesize $NH_4HCO_3$ at the manufacturing facility using $CO_2$ gas and $NH_4OH$ solution at much cheaper cost and thereby adding further cost savings.

This observation that $NH4HCO_3$ and $NH_4OH$ can be used as effectively as $KOH/K_2CO_3$ as a neutralizing agent is in contrast to the prior art teaching against the use of $NH_4OH$ as the neutralizing agent in succinic acid production. It has been reported that $NH_4OH$ is toxic to *E. coli* and it could cause a decrease in the viability of the cells and the succinate productivity (Andersson et al., 2009).

As a neutralizing agent, $NH_4OH$ is used in the concentration range of 1M to 15 M. In the preferred embodiment, $NH_4OH$ is used in the concentration range of 2M to 9M. In the most preferred embodiment, $NH_4OH$ is used in the concentration range of 6M to 8M.

Along with $NH_4OH$ as the neutralizing agent, a source of inorganic carbon is also provided. Any of the commercially available inorganic carbonate or bicarbonate salts can be used as a source of inorganic carbon. The inorganic salts useful as a source of inorganic carbon include sodium carbonate, sodium bicarbonate, magnesium carbonate, magnesium bicarbonate, potassium carbonate, potassium bicarbonate, ammonium carbonate, and ammonium bicarbonate. The bicarbonate salts are preferred over the carbonate salts. Among the bicarbonate salts, ammonium bicarbonate is preferred for the reasons of cost saving and cost recovery.

The inorganic carbonate and bicarbonate salts can be used in the range of 0.1 M to 6 M. In the preferred embodiment, $NH_4HCO_3$ is used in the concentration range of 0.1M to 5 M. In the most preferred embodiment, $NH_4HCO_3$ is used in the concentration range of 2 M to 4 M. The molar ratio between $NH_4OH$ and $NH_4HCO_3$ is in the range of 8:1 to 1:1. The preferred molar ratio between $NH_4OH$ and $NH_4HCO_3$ is in the ration of 6:1 to 2:1. The most preferred molar ratio between $NH_4OH$ and $NH_4HCO_3$ is in the ratio of 3:1 to 2:1.

The ratio of 8:3 between $NH_4OH$ and $NH_4HCO_3$ is the most preferred in the production of succinic acid using bacterial biocatalysts.

The ammonium hydroxide and ammonium bicarbonate solution can be prepared separately and supplied to the fermentor independent of each other. Ammonium hydroxide is supplied when it is required to maintain the pH of the fermentation medium in the near neutral range. Ammonium bicarbonate solution can be added at the beginning or supplied when required. In a preferred embodiment, the ammonium hydroxide and ammonium bicarbonate solution are preferred as a single combined solution and added to the fermentor when it is required to maintain the pH of the fermentation medium.

The mixture of $NH_4OH$ and $NH_4HCO_3$ can be prepared by dissolving ammonium bicarbonate salt in the ammonium hydroxide solution. In a preferred embodiment, the mixture of $NH_4OH$ and $NH_4HCO_3$ can be prepared by means of capturing carbon dioxide gas emanating from any industrial facility and there by contributing to the global efforts towards reducing carbon emission through carbon sequestration.

It is also possible to supplement the addition of solid inorganic carbon to the medium with a supply of carbon dioxide gas. The carbon dioxide can be sparged through the fermentor at a rate of 0.01 volume per volume per minute (vvm) to 1.0 vvm. In a preferred embodiment, the carbon dioxide gas is applied at the rate of 0.05 vvm to 0.5 vvm. In the most preferred embodiment, the carbon dioxide gas is applied at the rate of 0.1 vvm.

The list of the bacterial species suitable for development as a biocatalyst for the fermentative production of organic acids according to this invention includes *Escherichia coli, Gluconobacter oxydans, Gluconobacter asaii, Achrmobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp.* CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp.* ATCC 15592, *Rhodococcus sp.* ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serrtia marcescens, Salmonella typhimurium, Salmonella schottmulleri, Xanthomonas citri, Bacillus subtilis, Bacillus licheniformis, Bacillus amylolliquefaciens* and so forth. The yeast species selected from the following genera are also suitable for development of biocatalyst for the production of organic acids including succinic acid: *Saccharomyces, Kluyveromyces, Candida, Zygosaccharomyces, Torulopsis, Torulospora, Williopsis, Issatchenkia, Pichia, Schizosaccharomyces, Phaffia, Cryptoccus, Yarrowia,* and *Sacchamromycopsis.* These strains of microorganisms can be grown in the medium with a source of organic carbon and inorganic carbon compounds as described here.

As defined in this invention, the term biocatalyst includes microorganisms that have been developed for the purpose of manufacturing organic acid including succinic acid using biological feedstocks and inorganic carbon.

The microbial organisms of the present invention are grown in a number of different culture medium well known in the field of microbiology. For example, different strains of *E. coli* selected for succinic acid production are grown in Luria-Bertani (LB) medium containing 1% (w/v) tryptone, 0.5% (w/v) yeast extract, and 0.5% (w/v) NaCl. For the commercial production of the organic acid using fermentative processes involving a genetically modified microorganism as biocatalyst, a minimal mineral salt medium supplemented with a carbon source is preferred. The use of a minimal mineral salt medium as opposed to a rich medium like LB medium reduces the cost for the production of organic acids in a commercial scale. The minimal mineral mediums suitable for the present invention include NBS medium (Causey et al., 2007) and AM1 medium (Martinez et al., 2007). The NBS medium contains 1 mM betaine, 25.72 mM $KH_2PO_4$, 28.71 mM $K_2HPO_4$, 26.50 mM $(NH_4)_2HPO_4$, 1 mM $MgSO_4.7H_2O$, 0.1 mM $CaCl_2.2H_2O$, 0.15 mM Thiamine HCl, 5.92 µM $FeCl_36H_2O$, 0.84 µM $CoCl_2.6H2O$, 0.59 µM $CuCl_2.2H_2O$, 1.47 µM $ZnCl_2$, 0.83 µM $Na_2MoO_4$ $2H_2O$, and 0.81 µM $H_3BO_3$. The AM1 medium contains 1 mM betaine, 19.92 mM $(NH_4)_2HPO_4$, 7.56 mM $NH_4H_2PO_4$, 1.5 mM $MgSO_4.7H_2O$, and trace elements including 8.88 µM $FeCl_36H_2O$, 1.26 µM $CoCl_2.6H2O$, 0.88 µM $CuCl_2.2H_2O$, 2.20 µM $ZnCl_2$, 1.24 µM $Na_2MoO_42H_2O$, 1.21 µM $H_3BO_3$ and 2.50 µM $MnCl_24H_2O$. Corn steep liquor can be used in place of yeast extract and peptone. It is a byproduct from the corn wet-milling industry. When compared to the yeast extract and peptone, it is an inexpensive source of vitamins and trace elements.

In certain bacterial fermentations, it is necessary to have potassium ion in the growth medium. The potassium can be provided either in the form of KCl, or $KHCO_3$ or $KH_2PO_4$. These potassium salts can be used in the range of 1 mM to 100 mM. It is preferable to use $KH_2PO_4$ at 10 mM concentration for the reasons of cost saving.

The mineral medium for microbial growth is supplemented with both an organic and inorganic carbon source. Suitable fermentation broths for use in the present process preferably include at least about 208 g/L or at least about 30 g/L or at least about 40 g/L of one or more carbohydrate and/or sugar containing sources. More preferably, the fermentation broth includes at least about 70 g/L and most preferably, at least 120 g/L of the carbohydrate and/or sugar containing sources. The organic carbon sources useful in the present invention include but not limited to pentose sugars like xylose, and hexose sugars like glucose, fructose, galactose and glycerol. The organic carbon source is also be satisfied by providing a combination of different sugars such as a combination of glucose and xylose. The carbon source can also be derived from a hydrolysis of starch or lignocellulose. The hydrolysis of complex carbohydrates such as starch and lignocelluloses is achieved either by using thermo-chemical conversion processes or enzymatic methods well known in the art. For example, the hexose sugars suitable for the fermentation process of the present invention can be derived from grain sorghum flour through enzyme digestion. The preferred carbon source for the industrial production of organic acid using microbial fermentation is lignocellulosic hydrolysate derived from the hydrolysis of agricultural or forestry wastes. The lignocellulosic hydrolysate is further fractionated to yield a hexose-enriched and a pentose-enriched fraction and those fractions serve as the source of carbon for the commercial production of the organic acids using microbial fermentation processes. The lignocellulosic hydrolysate is further detoxified to remove certain chemicals such as furfural which are found to be toxic to a number of microbial organisms above certain concentrations.

A nitrogen providing compound is also supplied in the fermentation broth of the present invention as a nitrogen source for the organic acid producing microorganism to begin growth and start the fermentation process. Nitrogen producing compounds may include ammonium phosphate, urea or any other suitable compound containing nitrogen. The nitrogen producing compound may be present by weight in an amount of between about 0.1% and 10%, and more preferably between about 0.15% and 5%, and most preferably between about 0.18% and 3%.

Fermentation reaction vessels of any suitable, known type may be employed in performing the fermentation process of the present invention. The size of the fermentors suitable for the present invention is in the range of 3 L to 400,000 L. A variety of reactor configurations including packed bed reactors, continuous stirred tank reactors, rotating biological contact reactors, sequencing batch reactors and fluidized bed reactors may be used in the present process. The fermentation can be carried out by any known methods in the field of industrial microbiology and biotechnology. For example, the fermentation can be carried out in a continuous process or a batch mode or a fed-batch mode. The fed-batch mode of fermentor operation is preferred.

Further improvements in the yield and productivity of the desired organic compounds in the microorganisms selected for efficient carbon uptake and utilization capacities is achieved by manipulating appropriate fermentation parameters. The microorganisms suitable for the practice of the present invention are grown aerobically (in the presence of oxygen) or anaerobically (in the complete absence of oxygen). In one embodiment, the microorganisms suitable for the present invention are grown in a dual-phase growth regime, wherein the microorganism is initially grown in aerobic growth condition to reach a certain level of cell mass before transferring it to the anaerobic growth condition to achieve the production of required organic acids in commercially significant quantities. Cell mass was estimated by measuring the optical density at 550 nm ($OD_{550nm}$) using a spectrophotometer. During the production phase, the concentration of dissolved oxygen is maintained at approximately zero. This can be achieved either by means of sparging the fermentation vessel with carbon dioxide or nitrogen gas. The dissolved oxygen concentration is measured using a Clark-type oxygen electrode with gas permeable membrane.

The inventors have surprisingly found that by means of providing a minimal amount of oxygen during the production phase, the yield and productivity of the organic compounds is further improved. With the microaerobic condition during the production phase, there is a better utilization of organic carbon present in the medium as opposed to utilization of only 80% of the organic carbon under strict anaerobic condition during the production phase. The enhanced carbon utilization during microaerobic production phase is further accompanied by a noticeable increase in the yield and productivity of the organic compound.

The microaerobic condition can be achieved by means of mixing the air in appropriate amount with a carrier gas. Alternatively an appropriately low flow rate of air can be sparged. The oxygen level in the fermentation fluid can be monitored using an oxygen electrode or any other suitable device and the flow rate of the gas mix is adjusted to assure that the level of oxygen in the fermentation fluid is maintained at a constant level.

Microaeration rate suitable for the present invention is in the range of 0.0001 vvm to 0.1 vvm, preferably from about 0.001 to about 0.025 vvm, and even more preferably about 0.001 to about 0.0025 vvm with reference to the air used in the microaeration. Aeration is preferably done under conditions such as sparging that promotes the formation of fine gas bubbles. Agitation is preferably maintained.

The concentration of various organic acids and sugars are measured by HPLC. Succinic acid and other organic acids present in the fermentation broth are analyzed on Agilent 1200 HPLC apparatus with BioRad Aminex HPX-87H column. BioRad Microguard Cation $H^+$ is used as a guard column. The standards for HPLC analysis are prepared in 0.008N sulfuric acid. The HPLC column temperature is maintained at 50° C. Sulfuric acid at 0.008N concentration is used as a mobile phase at the flow rate of 0.6 ml/min. Quantification of various components is done by measuring their absorption at 210 nm. The HPLC technology is also helpful in determining the purity of the organic acid produced by the selected clones.

Example 1

Preparation of Solid Inorganic Carbon Source

A stock solution containing both ammonium hydroxide and ammonium bicarbonate was prepared by means of sequestering carbon dioxide in the solution of ammonium hydroxide (FIG. 1). One liter of 28-30% ammonium hydroxide solution was added to a 3 liter NBS (New Brunswick Scientific) fermentor and carbon dioxide gas was microsparged at the rate of 1L/minute. The ammonium hydroxide solution inside the fermentor was stirred at 500 rpm for an hour. At the end of one hour, the temperature of the fermentor had increased to 39.3° C. from an initial temperature of 19.5° C. Cooling of the fermentor was initiated by circulating cold water through a coil within the fermentor. With the cold water circulation the temperature of the fermentor reached 16.2° C. in about 2 hours. When the solution turned into a white slimy liquid, 325 ml of water was added to obtain approximately 11 M combined solution of ammonium with approximately 3 M bicarbonate. 11 M concentration of combined ammonium bicarbonate and ammonium hydroxide solution is an estimate based on the initial volume of 1 L of 14.5 M NH$_4$OH plus 325 ml of water added to get the precipitated bicarbonate back into solution. It is based on the assumption that the addition of CO$_2$ did not change the volume.

The combined ammonium hydroxide and ammonium bicarbonate solution obtained as described above was used in the fermentation of glucose in AM1 medium with the KJ122 strain of *E. coli* as a biocatalyst for the production of succinic acid in a total volume of 3,000 ml in a NBS fermentor maintained at 39° C. The fermentation medium also contained KH$_2$PO$_4$ (110 ml of 1M KH$_2$PO$_4$). The concentration of ammonium hydroxide was about 8N and the concentration of ammonium bicarbonate was about 3M. KJ122 inoculum had an initial OD$_{550nm}$ of 7.8 and 150 ml of this inoculum representing 5% (v/v) of the total fermentation volume was used. The pH was maintained at 6.7 and fermentation fluid was stirred with the impeller within the fermentor operated at 750 RPM. Glucose solution at the concentration of 650 g/L was fed as required. At the end of 36 hours of the production phase of fermentation, the succinic acid titer was 93.2 g/L and yield was 0.86 gram of succinic acid per gram of glucose consumed. The titer for acetic acid was 3.8 g/L.

Example 2

Succinic Acid Production with NH$_4$OH and NH$_4$HCO$_3$

Figure 2:
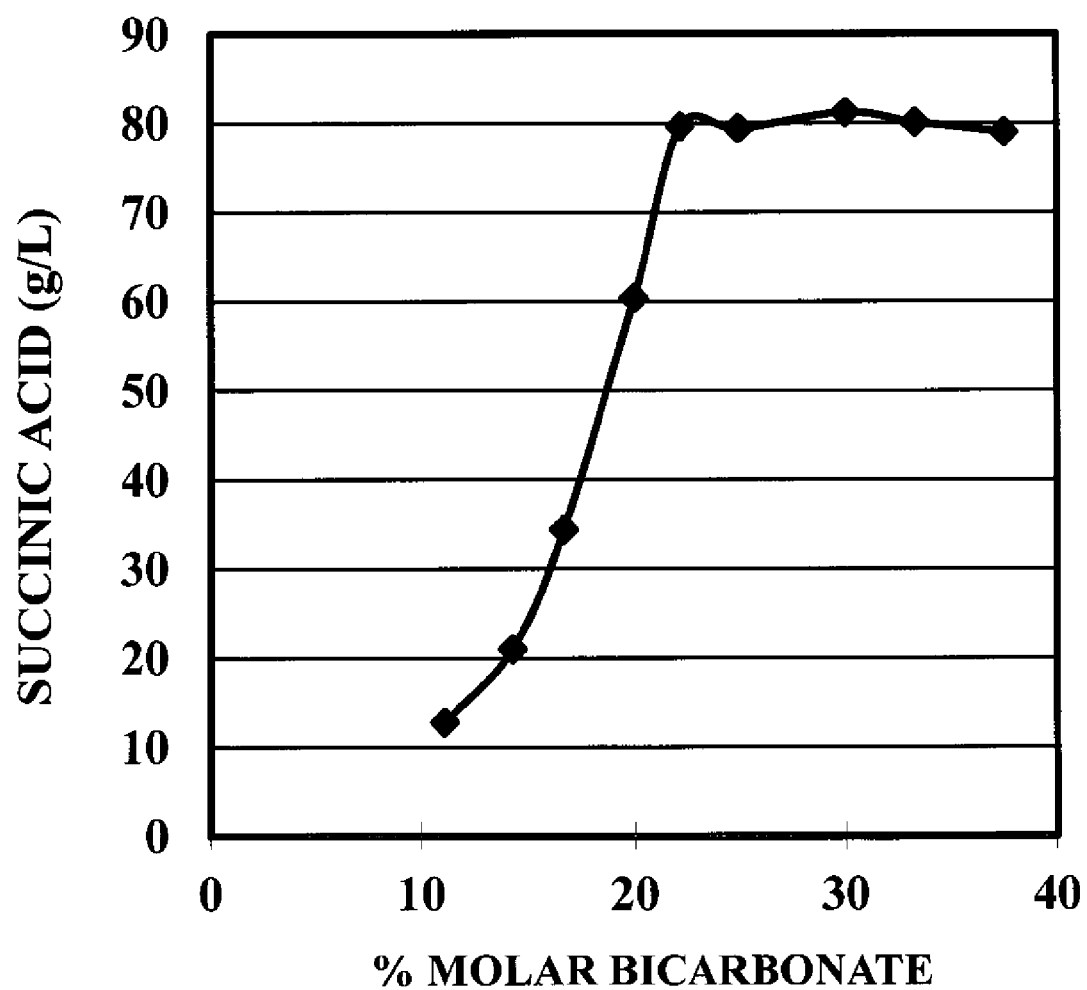
FIG. 2. Effect of increasing the bicarbonate concentration in the fermentation medium on succinic acid titer. The succinic acid titer in grams per liter (g/L) of fermentation broth is shown on the Y-axis. Shown on the x-axis is the % Molar bicarbonate concentration in the fermentation medium. The % Molar bicarbonate is the percentage of molar concentration of ammonium bicarbonate with reference to the molar concentration of total ammonium compounds present in the fermentation medium and include ammonium hydroxide used for neutralization and ammonium bicarbonate acting as a source of inorganic carbon.
Figure 3:
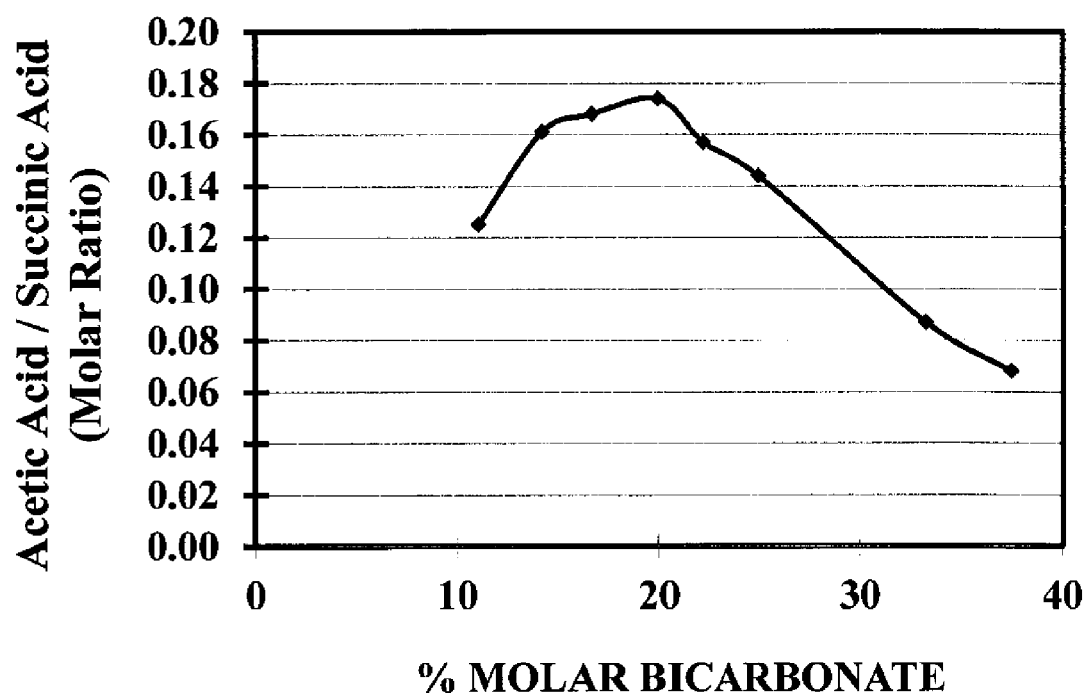
FIG. 3. Effect of increasing bicarbonate concentration in the fermentation medium on the molar ratio between acetic acid and succinic acid production. The values on the Y-axis are the molar ratio between acetic acid and succinic acid during fermentation in the presence of varying concentration of bicarbonate. Shown on the x-axis is the % Molar bicarbonate concentration in the fermentation medium. The % Molar bicarbonate is the percentage of molar concentration of ammonium bicarbonate with reference to the molar concentration of total ammonium compounds present in the fermentation medium and include ammonium hydroxide used for neutralization and ammonium bicarbonate acting as a source of inorganic carbon.

In order to identify the optimal ratio for NH$_4$OH and NH$_4$HCO$_3$ in the fermentative production of succinic acid, a series of succinic acid fermentations were conducted with varying ratios of NH$_4$OH and NH$_4$HCO$_3$. As shown in the Table 1 below, twelve different NH$_4$OH—NH$_4$HCO$_3$ compositions were tested in the succinic acid fermentation using the KJ122 strain of *E. coli* as a biocatalyst in a total volume of 2,000 ml in a NBS fermentor maintained at 39° C. The fermentation medium also contained KH$_2$PO$_4$ (55 ml of 1M KH$_2$PO$_4$), MgSO$_4$ (4 ml of 1.5 M MgSO$_4$), betaine (4 ml of 1M betaine), and trace elements. KJ122 inoculum had an initial OD$_{550nm}$ of 6.8 to 7.8 and 150 ml of this inoculum representing 7.5% (v/v) of the total fermentation volume was used. The pH was maintained at 6.5 and fermentation fluid was stirred with the impeller within the fermentor operated at 750 RPM. Glucose solution was fed as required. At the end of the fermentation the titers for succinic acid and acetic acid as well as the succinic acid yield were determined using HPLC technique. As the results shown in FIG. 2 indicate, the succinic acid titer showed a linear increase starting with the 10% molar bicarbonate concentration. The succinic acid titer reached a plateau after about 20% molar bicarbonate concentration. As defined in this invention, the % molar bicarbonate is the percentage of molar concentration of ammonium bicarbonate in the succinic acid fermentation medium with reference to the molar concentration of total ammonium compounds present in the fermentation medium. Thus if 8M NH$_4$OH and 1M NH$_4$HCO$_3$ are the only ammonium compounds present in the fermentation medium, the % molar bicarbonate value is 1/9=0.111 (11.1%). Also measured in this experiment was the molar ratio between the acetic acid and succinic acid in the fermentation broth with reference to increase in the % molar bicarbonate concentration in the fermentation medium. As the result shown in FIG. 3 indicates, once the succinic acid titer reaches a maximum value, any further increase in the % molar bicarbonate value caused a decrease in the titer for the acetic acid leading to a decrease in the ratio of acetic acid to succinic acid in the fermentation broth. The general observation from these fermentation runs was that in contrast to the prior art teaching against the use of NH$_4$OH and NH$_4$HCO3 as neutralizing agent and source of inorganic carbon in the succinic acid production respectively, commercially acceptable levels of succinic acid production was achievable using NH$_4$OH and NH$_4$HCO$_3$ in the fermentations medium for succinic acid production.

Example 3

Potassium Requirement in Succinic Acid Production

In this study efforts were made to determine whether potassium salts could be entirely eliminated from the fermentation medium without any significant effect on the succinic acid productivity. In the control experiment, the fermentation was carried out with an initial volume of 4,000 ml in AM1 medium using KJ122 as a biocatalyst. 3N NH$_4$OH and 0.75 M K$_2$CO$_3$, and 1.5 N KOH were used as the neutralizing base. Glucose was provided at the initial concentration of 102.9 grams per liter. At the end of 38 hours of fermentation, the glucose was completely utilized. At the end of 38 hours of fermentation, the succinic acid productivity was calculated to be 1.45 g/L/hr. In the second experiment, fermentation was carried out with 6N NH$_4$OH as the only neutralizing base in an initial volume of 2,000 ml. K$_2$CO$_3$ and KOH were completely eliminated from the fermentation medium. Carbon dioxide gas was provided as the source of inorganic carbon at the rate of 1 vvm (volume/volume/minute; 2 liters per minute). Glucose was provided at an initial concentration of 98.4 grams/liter. At the end of 70 hours of fermentation, the medium contained 2.8 grams of glucose/liter suggesting that the glucose consumption was not complete even after 70 hours of fermentation when there was no potassium in the fermentation medium. The succinic acid productivity for this fermentation without any added potassium was found to be 0.84 g/L/hr.

Based on the result of the fermentation experiments conducted without the addition of any potassium, another set of fermentations were conducted to test the ability of 10 mM KCl to satisfy the requirement for potassium in the succinic acid fermentation. In this set of experiment the ability of 10 mM KCl to replace 100 mM KHCO$_3$ in the fermentation medium was tested. In the control experiment, fermentation was carried out in an initial volume of 3,000 ml in AM1 medium with 150 ml of 2M KHCO$_3$ and 6N NH$_4$OH was used as neutralizing agent. Glucose was added at the initial concentration of 100 g/L. KJ122 strain of *E. coli* was used as the biocatalyst and the fermentation was conducted for a period of 36 hours. In another experiment conducted in parallel, fermentation was carried out in an initial volume of 1,500 ml in AM1 medium with 75 ml of 2M NH$_4$HCO$_3$ and 6N NH$_4$OH was used as the neutralizing agent. Glucose was added at the initial concentration of 100 g/L. KJ122 strain of *E. coli* was used as the biocatalyst and the fermentation was conducted for a period of 36 hours. Samples were drawn out from both the experiments and the amount of glucose, succinic acid, acetic acid, pyruvic acid, malic acid, and lactic acid in the fermentation broth were determined using HPLC technique.

Figure 4:
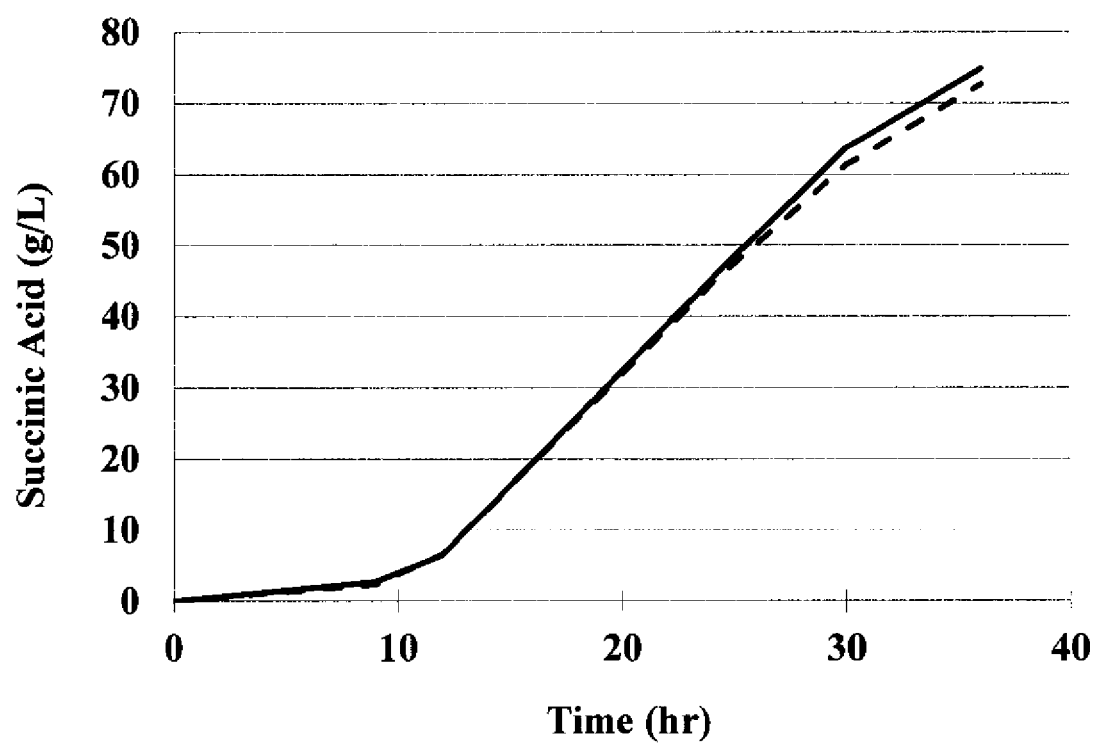
FIG. 4. Normalized succinic acid titer in grams/liter (g/L) in the fermentation medium containing 100 mM $NH_4HCO_3$ and 10 mM KCl (solid line) or 100 mM $KHCO_3$ (broken line). The fermentation was run for a period of 36 hours.
Figure 5:
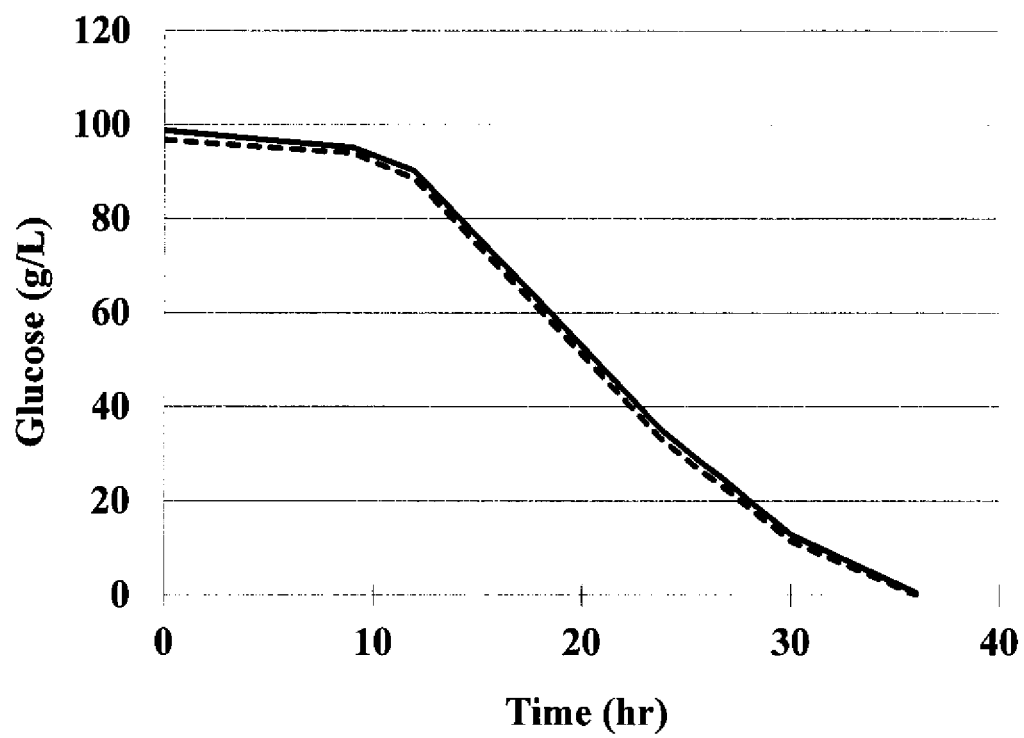
FIG. 5. Kinetics of glucose utilization in the fermentation medium containing 100 mM $NH_4HCO_3$ and 10 mM KCl (solid line) or 100 mM $KHCO_3$ (broken line). The glucose concentration in the growth medium is expressed as grams/liter (g/L). The fermentation was run for a period of 36 hours.
Figure 6:
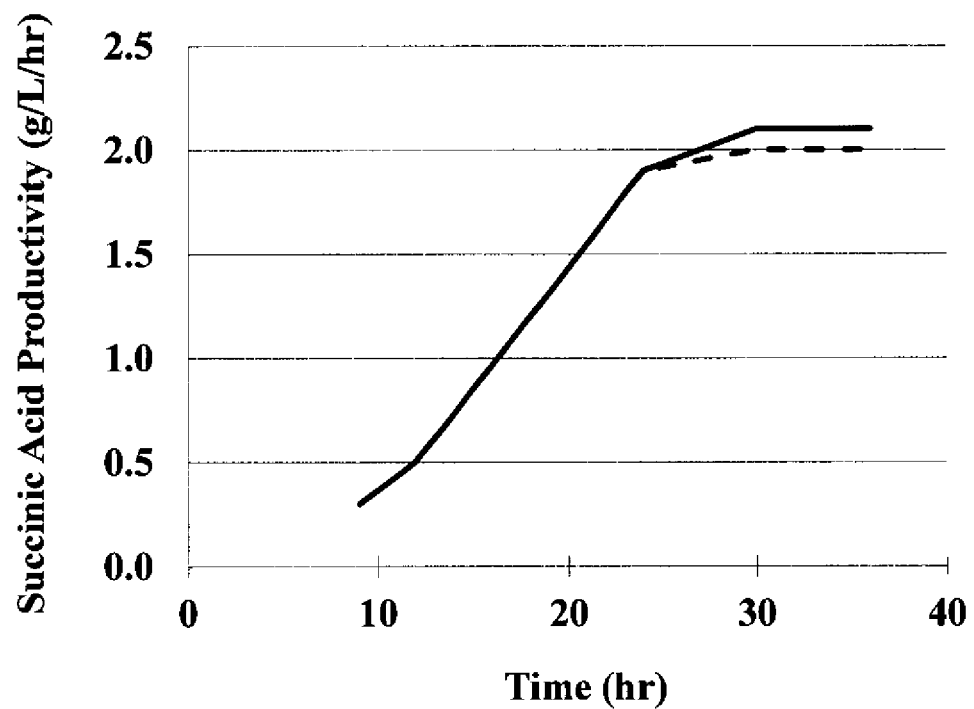
FIG. 6. Normalized cumulative succinic acid productivity in the fermentation medium containing 100 mM $NH_4HCO_3$ and 10 mM KCl (solid line) or 100 mM $KHCO_3$ (broken line). The normalized cumulative succinic acid productivity is expressed in terms of grams of succinic acid produced per liter per hour (g/L/hr). The fermentation was run for a period of 36 hours.

As the results shown in FIGS. 4 and 6 indicate succinic acid titer and succinic acid productivity in the samples derived from the fermentation runs containing 10 mM KCl and fermentation runs containing 100 mM KHCO$_3$ were very much comparable to each other. Moreover, as the results shown in FIG. 5 indicates, the rate of glucose consumption were also comparable between the fermentation run with 10 mM KCl and the fermentation run with 100 mM KHCO$_3$.

Figure 7:
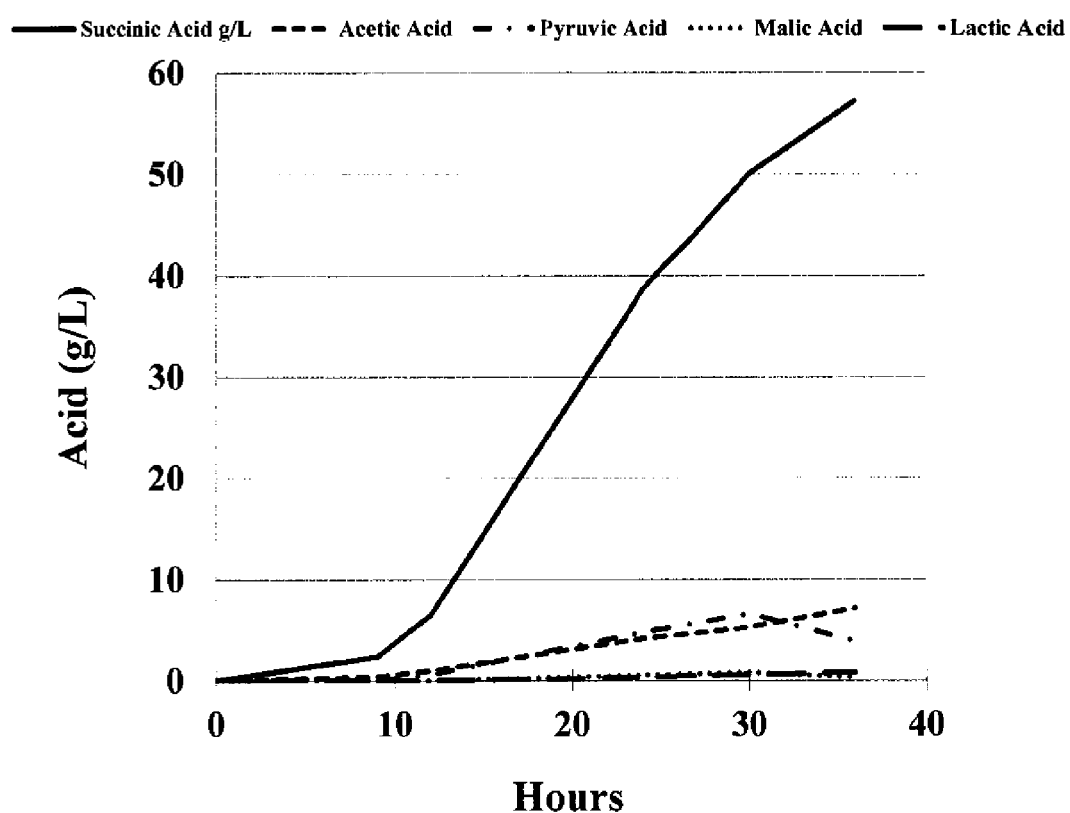
FIG. 7. Titer (g/L) for succinic acid, acetic acid, pyruvic acid, malic acid, and lactic acid in the fermentation medium containing 100 mM $KHCO_3$ as a source of potassium and inorganic carbon. The fermentation was run for a period of 36 hours.
Figure 8:
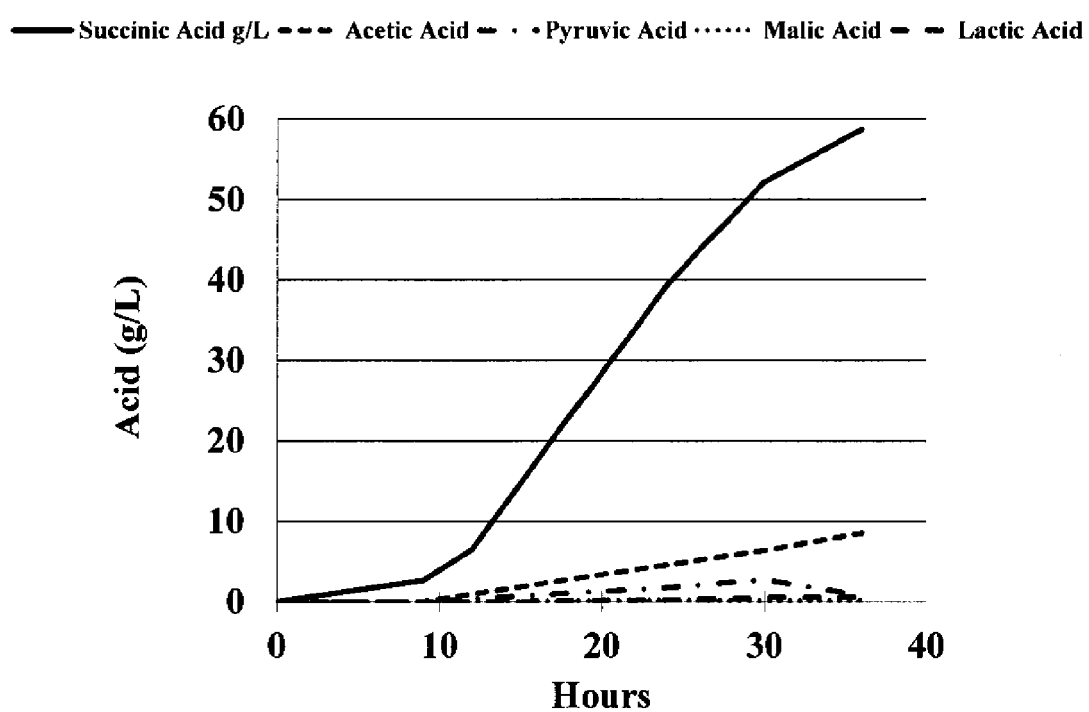
FIG. 8. Titer (g/L) for succinic acid, acetic acid, pyruvic acid, malic acid, and lactic acid in the fermentation medium containing 100 mM $NH_4CO_3$ as a source of inorganic carbon and 10 mM KCl as a source of potassium. The fermentation was run for a period of 36 hours.

The results shown in FIGS. 7 and 8 indicate that the composition of various organic acids produced in the fermentation runs with 100 mM KHCO$_3$ is very much comparable to the fermentation run with 10 mM KCl. Thus the substitution of KHCO$_3$ with NH$_4$HCO$_3$ did not alter the titer for succinic acid with reference to the titer of other organic acids produced as byproducts.

Example 4

Comparison of Batch and Fed-Batch Fermentation

There are several advantages associated with operating the fermentor in the fed-batch mode when compared to the batch mode operation. In the fed-batch mode, the biocatalyst is subjected to less osmotic stress as the sugar substrate is added gradually. Moreover, it is possible to avoid any potential waste in the organic carbon feedstock by means of feeding organic compounds only when it is required under fed-batch mode. In the case of batch mode of fermentation, the entire amount of organic carbon is added at the beginning of the fermentation and when the fermentation does not consume the organic carbon entirely, the left over organic carbon is in the waste stream at the end of the fermentation run. In order to determine whether the succinic acid production is comparable both in the fed-batch and batch mode of fermentor operations, parallel experiments were conducted both in the batch mode and in the fed-batch mode. In the fed-batch, the fermentation was conducted with an initial volume of 2,000 ml with 48 ml of 1M KH$_2$PO$_4$, 3.5 ml of 1.5 MgSO$_4$, 3.5 ml of 1 M Betaine and trace elements and neutralized with 7N NH$_4$OH and 3 M NH$_4$HCO$_3$. KJ122 biocatalyst was inoculated and the pH was maintained at 6.5. The fermentation fluid was stirred by operating the impeller within the fermentor at 750 rpm. The initial glucose concentration was 25 g/l and additional glucose was fed as required. In the fermentation conducted in the batch mode, the same medium was batched in 4,000 ml. 150 ml KJ122 biocatalyst was inoculated and the pH was maintained at 6.5. The fermentation fluid was stirred by operating the impeller within the fermentor at 750 rpm. Glucose was added at the initial concentration of 100 g/l.

Figure 9:
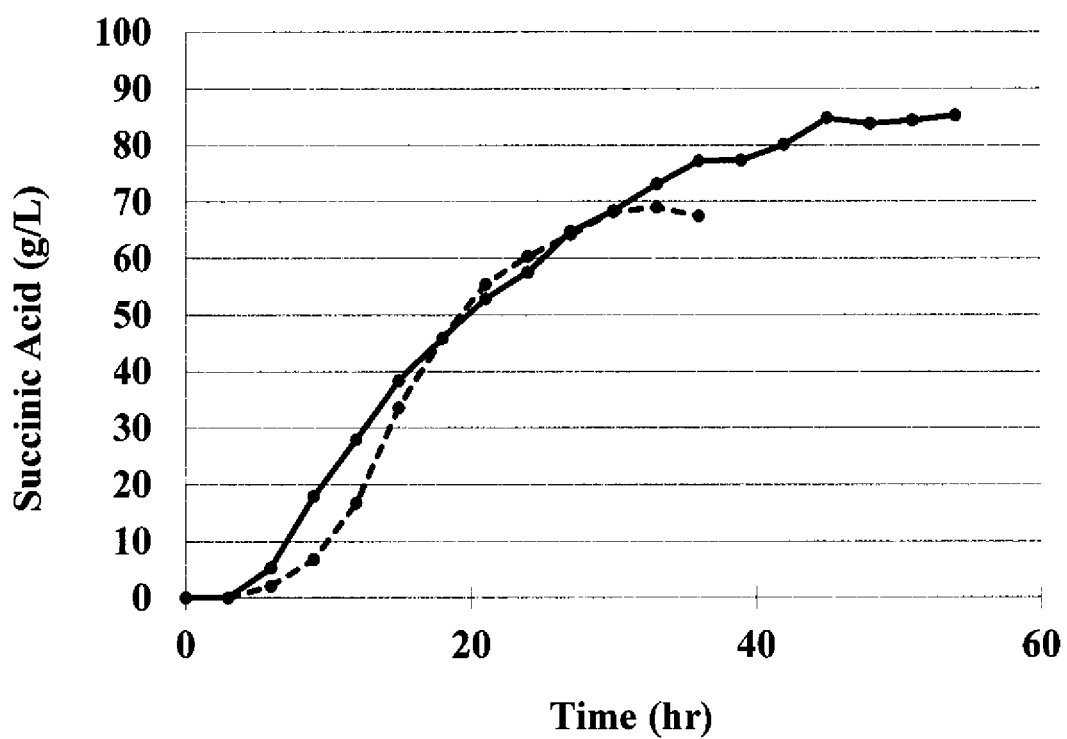
FIG. 9. Kinetics of production of succinic acid under fed-batch mode (solid line) and batch mode (broken line) of fermentation. 7N $NH_4OH$ and 3M $NH4HCO_3$ were used as the source of neutralizing agent and source of inorganic carbon respectively. KJ22 strain of *E. coli* was used as the biocatalyst.
Figure 10:
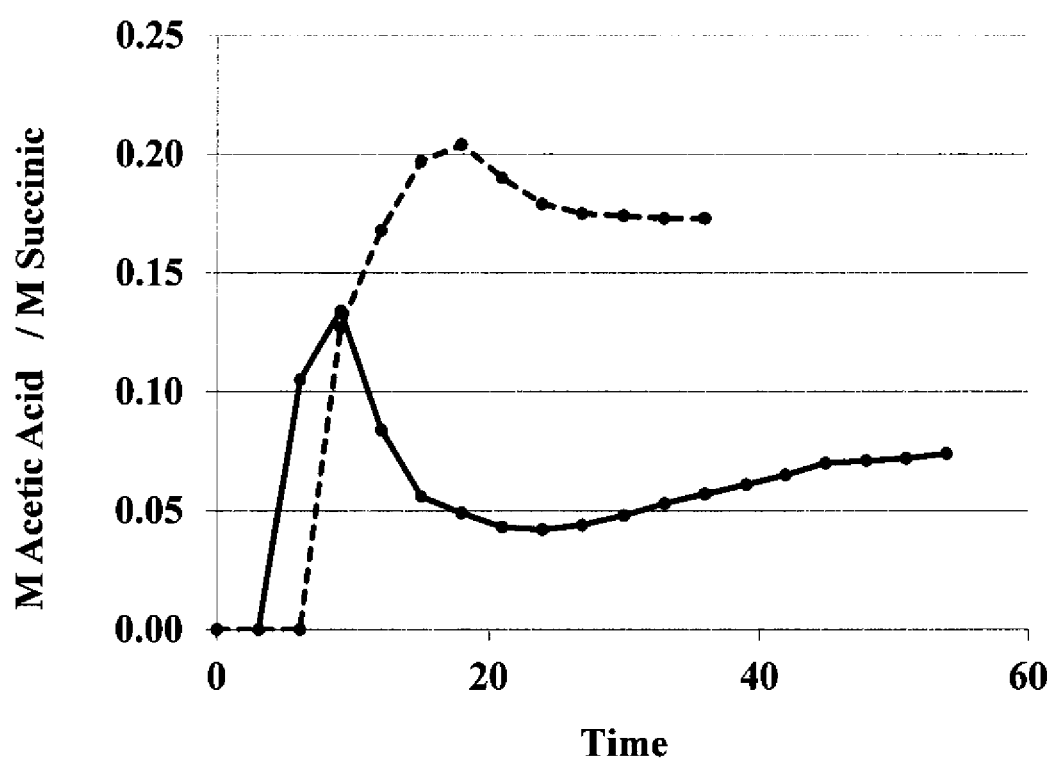
FIG. 10. The molar ratio between acetic acid and succinic acid production during fed-batch mode (solid line) and batch mode (broken line) of succinic acid fermentation. 7N $NH_4OH$ and 3M $NH_4HCO_3$ were used as the source of neutralizing agent and source of inorganic carbon respectively. KJ122 strain of *E. coli* was used as the biocatalyst. Under fed-batch mode of fermentation, the ratio of acetic acid produced to succinic acid produced was found to be lower during most of production phase indicating the production of acetic acid as a byproduct is much lower under fed-batch mode of fermentation when compared to the acetic production under batch mode of fermentation.

The productivity and the relative ratio between acetic acid and succinic acid were measured under both fermentation conditions. As the result shown in FIG. 9 indicates, the succinic acid titer was comparable between batch and fed-batch modes of fermentation. The succinic acid titer in the fed-batch fermentation was 85.2 gram/l while the titer for acetic acid was 3.2 g/l. On the other hand, in the batch mode, the succinic acid titer was 67.1 g/l and acetic acid titer was 5.3 g/L. The yield of succinic acid was 80.2 grams of succinic acid per gram of glucose consumed in the fed-batch as compared to the succinic acid yield of 71.8 grams of succinic acid per gram of glucose consumed in the batch mode. In addition, it was surprisingly noticed that the acetic acid to succinic acid ratio was lower in the fed-batch mode of fermentation when compared to the acetic acid to succinic acid ratio in the batch mode of fermentation (FIG. 10).

Example 5

Microaeration of Fermentation Vessel

Figure 11:
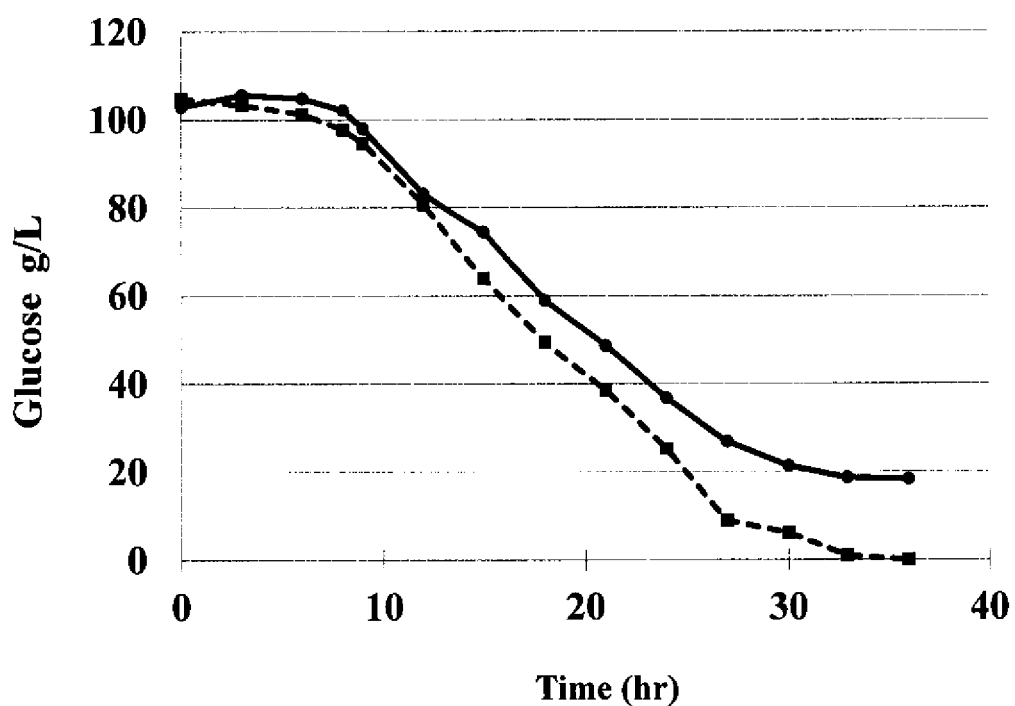
FIG. 11. Kinetics of glucose consumption in the control succinic acid fermentation maintained under anaerobic condition (solid line) and microaerated succinic acid fermentation (broken line). The fermentations were carried out for 36 hours. At the end of 36 hours of fermentation, glucose was completely consumed in the microaerated samples while nearly 20 g/L of glucose remained in the fermentation samples maintained under anaerobic condition. Ammonium hydroxide and ammonium bicarbonate were used as neutralizing and source of inorganic carbon respectively. Microaeration was provided by supplying air at the rate of 0.1 vvm.
Figure 12:
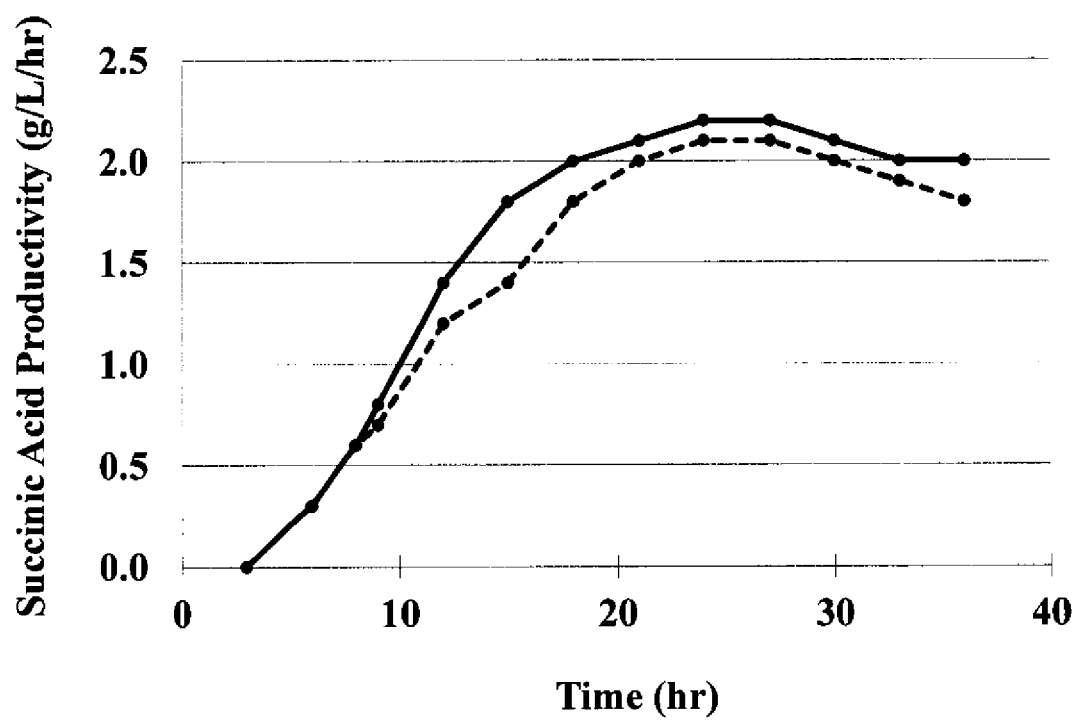
FIG. 12. Normalized cumulative succinic acid productivity (g/L/hr) in the fermentation conducted under strict anaerobic conditions (broken line) and in the fermentation conducted under microaerobic condition (solid line). The fermentation was conducted for 36 hours. Ammonium hydroxide and ammonium bicarbonate were used as neutralizing and and source of inorganic carbon respectively. Microaeration was provided by supplying air at the rate of 0.1 vvm.

Since glucose consumption in the absence of potassium does not go to completion, efforts were made to determine whether providing microaeration would enhance the fermentation. In the control experiment, fermentation was carried out in a total volume of 9,000 ml with 6N NH$_4$OH as the neutralizing base. 100 mM NH$_4$HCO$_3$ was provided as the source of inorganic carbon. Additional inorganic carbon source was provides by supplying carbon dioxide at the rate of 0.1 vvm. KJ122 biocatalyst was inoculated at the initial OD$_{550nm}$ of 6.2 and the pH was maintained at 6.75. Fermentation fluid was stirred by operating the impeller within the fermentor at the rate of 550 rpm. Initial glucose concentration was 102.9 grams/L. The glucose and succinic acid concentrations were measured using HPLC techniques. In a parallel experiment, fermentation was carried out in a total volume of 18,000 ml with 6N NH$_4$OH as the neutralizing base. 100 mM NH$_4$HCO$_3$ was provided as the source of inorganic carbon. Additional inorganic carbon source was provided by supplying carbon dioxide mixed with 1% air (99% CO2/1% air) at the rate of 0.1 vvm. KJ122 biocatalyst was inoculated at the initial OD$_{550nm}$ of 6.1 and the pH was maintained at 6.75. Fermentation fluid was stirred by operating the impeller within the fermentor at the rate of 300 rpm. Initial glucose concentration was 104.7 grams/L. In the fermentation run supplied only with carbon dioxide, at the end of 36 hours of fermentation, nearly about 20% of the initially added glucose was still present while in the fermentation run supplied with carbon dioxide gas containing 1% air, the glucose consumption was complete by 36 hour (FIG. 11). In addition, as the result shown in FIG. 12 indicates, the succinic acid productivity was slightly higher in the microaerated sample when compared to the control sample.

Figure 13:
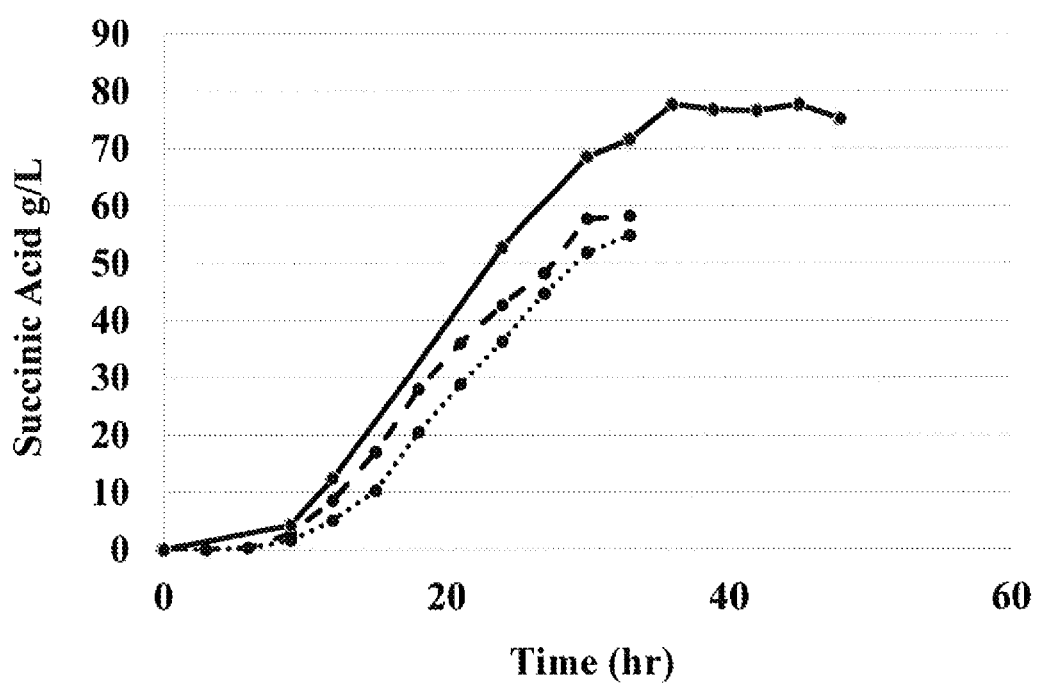
FIG. 13. Normalized succinic acid titer (g/L) in the succinic acid fermentations aerated with different amounts of air mixed with carbon dioxide gas. The fermentor was supplied with carbon dioxide gas mixed with air at 3% (dotted line), 2% (broken line) or at 0.5% (solid line). Ammonium hydroxide was used as neutralizing agent.
Figure 14:
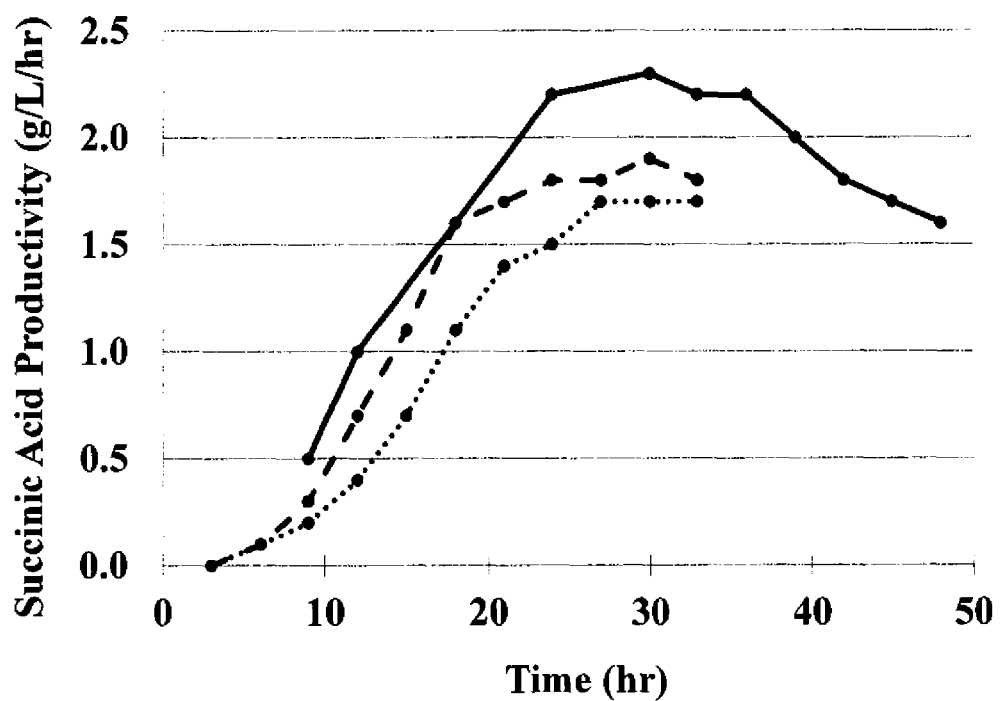
FIG. 14. Normalized cumulative succinic acid productivity (g/L/hr) in the succinic acid fermentations aerated with different amounts of air mixed with carbon dioxide gas. The carbon dioxide supply to fermentor was mixed with air at 3% (dotted line), 2% (broken line) or at 0.5% (solid line). Ammonium hydroxide was used as neutralizing agent.

In the next set of experiments, efforts were made to compare the effect of different levels of microaeration on fermentation profile. In these experiments, fermentation was run with 6N NH$_4$OH as the neutralizing base. The pH of the fermentation vessel maintained at 6.75 and the fermentation temperature was kept at 37° C. Glucose was provided as the source of organic carbon at the concentration of 100 g/L. 100 mM KHCO$_3$ was provided as the source of inorganic carbon. Additional source of inorganic carbon was provided by supplying carbon dioxide gas either alone or mixed with definite amount of air. Thus in a fermentation run with an initial volume of 9,000 ml, aeration was provided with carbon dioxide gas containing 3% air at the rate of 0.1 vvm and the impeller within the fermentor was operated at 550 rpm. In another fermentation run with an initial volume of 18,000 ml, aeration was provided at the rate of 0.1 vvm with carbon dioxide gas containing 2% air. The fermentation solution was stirred by operating the impeller within the fermentor at 300 rpm. In the third fermentation run with an initial volume of 27,000 ml, aeration was provided at the rate of 0.037 vvm with carbon dioxide gas containing 0.5% air. The fermentation fluid was stirred by operating the impeller within the fermentor at 200 rpm. As the results shown in FIGS. 13 and 14 indicate excess amounts of oxygen supply decreased both the titer and the productivity for succinic acid. Another notable advantage in microaerating the fermentation vessel was related to byproduct accumulation during succinic acid fermentation. With microaeration, it was possible to decrease the amount of byproducts such as pyruvic acid, malic acid, and lactic acid when compared to the levels of these byproducts in the fermentation with high oxygen supply (Table 2).

TABLE 1

Ratio of NH$_4$OH and NH$_4$HCO$_3$ tested to identify an optimal composition for succinic acid fermentation.

| Fermentation number | NH$_4$OH (M) | NH$_4$HCO$_3$ (M) | % Molar Bicarbonate* | Succinic Acid Titer (g/L) | Acetic Acid Titer (g/L) | Succinic Acid Yield (g/g) |
|---|---|---|---|---|---|---|
| 1 | 5 | 1 | 16.7 | 34.4 | 2.9 | 77.72 |
| 2 | 5 | 2 | 28.6 | 76.8 | 2.8 | 83.29 |
| 3 | 5 | 3 | 37.5 | 79.0 | 2.7 | 83.40 |
| 4 | 6 | 1 | 14.3 | 21.0 | 1.7 | 69.61 |
| 5 | 6 | 2 | 25 | 79.4 | 5.8 | 79.62 |
| 6 | 6 | 3 | 33.3 | 80.1 | 3.5 | 83.51 |
| 7 | 7 | 1 | 12.5 | 21.9 | 2.3 | 71.5 |
| 8 | 7 | 2 | 22.2 | 79.6 | 6.4 | 80.4 |
| 9 | 7 | 3 | 30 | 81.2 | 3.4 | 84.06 |
| 10 | 8 | 1 | 11.1 | 12.8 | 0.8 | 65.61 |
| 11 | 8 | 2 | 20 | 60.4 | 5.4 | 78.73 |
| 12 | 8 | 3 | 27.3 | 82.9 | 4.4 | 81.95 |

*% Molar Bicarbonate is the percentage of molar concentration of ammonium bicarbonate in the succinic acid fermentation medium with reference to the molar concentration of total ammonium compounds present in the fermentation medium.

TABLE 2

Succinic acid and other byproducts in 20 L fermentation runs with different levels of aeration

| Condition | Succinic acid (g/l) | Pyruvic acid (g/l) | Malic acid (g/l) | Acetic acid (g/l) | Lactic acid (g/l) | Yield (g/g) |
|---|---|---|---|---|---|---|
| Low O$_2$ (99.5% CO$_2$ + 0.5% Air) | 47.6 | 0 | 0.6 | 5.4 | 0 | 75.9 |
| High O$_2$ (97% CO$_2$ + 3% Air) | 44.7 | 7.3 | 8.3 | 4.6 | 0.4 | 62.2 |

REFERENCES

All references are listed for the convenience of the reader. Each reference is incorporated by reference in its entirety.

U.S. Pat. No. 5,168,055
U.S. Pat. No. 5,958,744
U.S. Pat. No. 6,117,404
U.S. Pat. No. 6,270,731
U.S. Pat. No. 6,455,284
U.S. Pat. No. 6,524,843
U.S. Pat. No. 6,908,507
U.S. Pat. No. 7,070,967
U.S. Pat. No. 7,223,567
U.S. Pat. No. 7,223,576
U.S. Pat. No. 7,232,664
U.S. Pat. No. 7,244,610
U.S. Pat. No. 7,256,016
U.S. Pat. No. 7,262,046
U.S. Pat. No. 7,514,056
U.S. Pat. No. 7,563,606
U.S. Pat. No. 7,596,952
U.S. Pat. No. 7,608,439
U.S. Patent Application Publication No. 2006/0073577
U.S. Patent Application Publication No. 2006/0185519
U.S. Patent Application Publication No. 2006/0193765
U.S. Patent Application Publication No. 2006/0205048
U.S. Patent Application Publication No. 2007/0111294
U.S. Patent Application Publication No. 2008/0072496
U.S. Patent Application Publication No. 2008/0293113
U.S. Patent Application Publication No. 2009/0162914
U.S. Patent Application Publication No. 2009/0170174
U.S. Patent Application Publication No. 2009/0186392
U.S. Patent Application Publication No. 2010/0051859
U.S. Patent Application Publication No. 2010/0092359
International Patent Application Publication No. WO 2009/083756
International Patent Application Publication No. WO 2010/115067
Andersson, C. (2007) Succinic acid production using metabolically engineered *Escherichia coli*. Licentiate Thesis. Lulea University of Technology (Master Thesis, Lulea University of Technology, and February 2007)
Andersson, C., Hodge, D., Berglund, K. A., Rova, U. (2007) Effect of different carbon sources on the production of succinic acid using metabolically engineered *Escherichia coli. Biotechnol. Prog.* 23: 381-388.
Andersson, C., Helmerius, J., Berglund, K. A., Rova, U. (2009) Inhibition of succinic acid production in metabolically engineered *Escherichia coli* by neutralizing agent, organic acids and osmolarity. *Biotechnol. Prog.* 25: 116-123.
Causey, T. B., Shamugam, K. T., Yomano, L. P., Ingram, L. O. (2004) Engineering *Escherichia coli* for efficient conversion of glucose to pyruvate. *Proc Natl Acad Sci USA* 101:2235-2240.
Grosz, R., Stephanopoulos, G. (1990) Physiological, biochemical, and mathematical studies of micro-aerobic continuous ethanol fermentation by *Saccharomyces cerevisiae*. III. Mathematical model of a cellular energetic and catabolism. *Biotechnol. Bioeng.* 36: 1030-1040.
Heux, S., Cachon, R., Dequin, S. (2006) Cofactor engineering in *Saccharomyces cerevisiae*: Expression of a H$_2$O-forming NADH oxidase and impact on redox metabolism. *Metab. Eng.* 8: 303-314.
Hojo, O. Hokka, C. O. and Major, A. M. (1999) Ethanol production by a flocculant yeast strain in a CSTR type fermentor with cell recycling. *Appl. Biochem Biotechnol.* 77-79: 535-545.
Hong, S. H., Kim, J. S., Lee, S. Y., In, Y. H., Choi, S. S., Rih, J. K., Kim, C. H., Jeong, H., Hur, C. G., and Kim, J. J. (2004) The genome sequence of the capnophillic rumen bacterium *Mannheimia succiniciproducens. Nat. Biotechnol.* 22: 1275-1281.
Hoppe, G. K., Hansford, G. S. (1984) The effect of micro-aerobic conditions on continuous ethanol production by *Saccharomyces cerevisiae. Biotech. Lett.* 6: 681-686.

Jantama, K, Haupt, M. J., Svoronos, S. A., Zhang, X., Moore, J. C., Shanmugham, K. T., Ingram, L. O. (2008a) Combining metabolic engineering and metabolic evolutions to develop nonrecombinant strains of *Escherichia coli* C that produce succinate and malate. *Biotechnol Bioeng* 99: 1140-1153.

Jantama, K., Zhang, X., Moore, J. C., Shanmugam, K. T., Svoronos, S. A., Ingram, L. O. (2008b) Eliminating side products and increasing succinate yields in engineered strains of *Escherichia coil* C. *Biotechnol Bioeng* 101: 881-893.

Lawford, H. G., Rousseau, J. D. (1994) Effect of oxygen on ethanol production by a recombinant ethanolgenic *E. coli*. *Appl. Biochem. Biotechnol.* 45: 349-366.

Lee, P., Lee, S., Hong, S. and Chang, H. (2002) Isolation and characterization of a new succinic acid-producing bacterium, *Mannheimia succiniproducens* MBEL55E, from bovine rumen. *Appl. Microbiol. Biotechnol.* 58: 663-668.

Liden, G., Frazen, C. J., Niklasson, C. (1994) A new method for studying microaerobic fermentations. I. A theoretical analysis of oxygen programmed fermentation. *Biotechnol. Bioeng.* 44: 419-427.

Lin, H., San, K-Y., and Bennett, G. N. (2005) Effect of *Sorghum vulgare* phosphoenolpyruvate carboxylase and *Lactococcus lactis* pyruvate carboxylase coexpression on succinate production in mutant strains of *Escherichia coli*. *App. Microbiol. Biotechnol.* 67: 515-523.

Lu, S., Eiteman, M. A. and Altman, E. (2009) Effect of CO2 on succinate production in dual-phase *Escherichia coli* fermentations. *J. Biotechnol.* 143: 213-223.

Martinez, A., Grabar, T. B., Shanmugam, K. T., Yomano, L. P. York, S. W., Ingram, L. O. (2007) Low Salt medium for lactate and ethanol production by recombinant *Escherichia coli* B. *Biotechnol Lett.* 29: 397-404.

Okuda, N., Ninomiya, K., Takao, M. and Shioya, S. (2007) Microaeration enhances productivity of bioethanol from hydrolysate of waste house wood using ethanolgenic *Escherichia coli* KO11. *J. Biosci Bioeng.* 103:350-357.

Price, G. D., Woodger, F. J., Badger, M. R., Howitt, S. M., and Tucker, L. (2004) Identification of a SulP-type bicarbonate transporter in marine cyanobacteria. *Proc. Natl. Acad Sci, USA.* 101: 18228-18233.

Price, G. D., Badger, M. R., Woodger, F. J. and Long, B. M. (2008) Advances in understanding the cyanobacterial CO2-concentrating-mechanism (CCM): functional components, Ci transporters, diversity, genetic regulation and prospects for engineering into plants. *J. Exp. Bot.* 59: 1441-1461.

Rudolf, A., Baudel, H., Zacchi, G., Hahn-Hagerdal, B., and Liden, G. (2008) Simultaneous saccahrification and fermentation of steam-pretreated bagasse using *Saccharomyces cerevisae* TMB3400 and *Pichia stipitis* CBS6054. *Biotechnol. Bioeg.* 99:783-790.

Sanchez, A. M., Bennett, G. N. and San, K. Y. (2005) Efficient succinic acid production form glucose through overexpression of pyruvate carboxylase in an *Escherichia coli* alcohol dehydrogenase and lactate dehydrogenase mutant. *Biotechnol Prog.* 21: 358-365.

Sanchez, A. M., Bennett, G. N. and San, K-Y. (2005) Novel pathway engineering design of the anaerobic central metabolic pathway in *Escherichia coli* to increase succinate yield and productivity. *Metabolic Engineer.* 7: 229-239.

Song, H. and Lee, S. Y. (2006) Production of succinic acid by bacterial fermentation. *Enzyme and Microbial Technol.* 39: 352-361.

Song, H., Lee, J. W., Choi, S., You, J. K., Hong, W. H. and Lee, S. Y. (2007) Effects of dissolved CO2 levels on the growth of *Mannheimia succiniproducens* and succinic acid production. *Biotechnol. Bioengineer.* 15: 1296-304.

Spalding, M. H. (2008) Microalgal carbon-dioxide-concentrating mechanisms: *Chlamydomonas* inorganic carbon transporters. *J. Exp. Bot.* 59: 1463-1473.

Vemuri, G. N., Eiteman, M. A., Altman, E. (2002) Effects of growth mode and pyruvate carboxylase on succinic acid production by metabolically engineered strains of *Escherichia coli*. *App. Environ. Microbiol.* 68: 1715-1727.

Zhang, X., Jantama, K., Moore, J. C., Jarboe, L. R., Shanmugam, K. T., Ingram, L. O. (2009) Metabolic evolution of energy-conserving pathways for succinate production in *Escherichia coli*. *Proc Natl Acad Sci USA* 106: 20180-20185.

Zhang, X., Shen, Y., Shi, W. and Bao, X. (2010) Ethanolic confermenttion with glucose and xylose by the recombinant industrial strain *Saccharomyces cerevisiae* NAN-127 and the effect of furfural on xylitol production. *Bioresour. Technol.* 101: 7104-7110.

Zheng, Z., Guo, N., Hao, J., Cheng, K. Sun. Y., Liu, D. (2009) Scale-up of micro-aerobic 1,3-propanediol production with *Klebsiells pneumonia* CGMCC 1.6366. *Process Biochem.* 44: 944-948.

What is claimed is:

1. A method for producing succinic acid through fermentation comprising the steps of:
providing a biocatalyst based on a non-naturally occurring, genetically altered *Escherichia coli* bacterium for succinic acid production;
providing a source of organic carbon in a minimal medium;
providing a source of neutralizing agent;
providing a source of inorganic carbon; and
maintaining the biocatalysts under microaerobic condition during the production phase wherein the microaerobic condition is provided by supplying a gas mixture containing carbon dioxide and air wherein said gas mixture contains at least 99 percent carbon dioxide and less than 1 percent air and said gas mixture is fed at the flow rate of at least 0.001 vvm.

2. The method for producing succinic acid according to claim 1, wherein said source of neutralizing agent is ammonium hydroxide.

3. The method for producing succinic acid according to claim 1, wherein said source of inorganic carbon is ammonium bicarbonate.

4. The method for producing succinic acid according to claim 1, wherein said source of neutralizing agent is ammonium hydroxide and said source of inorganic carbon is ammonium bicarbonate.

5. The method for producing succinic acid according to claim 1, wherein the biocatalyst has an enhanced ability for inorganic carbon uptake.

6. The method for producing succinic acid according to claim 5, wherein the enhanced ability for inorganic carbon uptake results from a genetic modification that increases inorganic bicarbonate transport activity.

7. The method for producing succinic acid according to claim 5, wherein the enhanced ability for inorganic carbon uptake of the biocatalyst results from a genetic modification to one of the carboxylating enzyme present within the biocatalyst.

8. The method for producing succinic acid according to claim 1, wherein the fermentation is run in a batch mode.

9. The method for producing succinic acid according to claim 1, wherein the fermentation is run in a fed-batch mode.

10. The method of producing succinic acid as in claim 1, wherein the organic carbon source is derived from the hydrolysis of a plant derived carbohydrate.

11. The method of producing succinic acid as in claim 1, wherein the organic carbon is derived from the hydrolysis of starch from grain sorghum.

12. The method of producing succinic acid as in claim 1, wherein the organic carbon is derived from the hydrolysis of lignocellulosic feed stock.

13. The method for producing succinic acid as in claim 4, wherein the ammonium hydroxide and ammonium bicarbonate solution are mixed together in advance and provided to the fermenter through a single feed line.

14. The method for producing succinic acid as in claim 4, wherein the ammonium hydroxide and ammonium bicarbonate are used in the molar ratio of 8:1 to 1:1.

15. The method for producing succinic acid as in claim 4, wherein the ammonium hydroxide and ammonium bicarbonate are used in the molar ratio of 4:1 to 2:1.

16. The method for producing succinic acid as in claim 4, wherein the ammonium bicarbonate is prepared by trapping carbon dioxide gas in ammonium hydroxide solution.

* * * * *